(12) United States Patent
Donovan et al.

(10) Patent No.: US 10,864,281 B2
(45) Date of Patent: *Dec. 15, 2020

(54) INCLUSION COMPLEXES AND METHODS FOR MAKING THE SAME

(71) Applicant: The Board of Trustees of the University of Illinois, Urbana, IL (US)

(72) Inventors: Joseph D. Donovan, Urbana, IL (US); Soo-Yeun Lee, Champaign, IL (US); Youngsoo Lee, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/145,416

(22) Filed: Sep. 28, 2018

(65) Prior Publication Data

US 2019/0099501 A1 Apr. 4, 2019

Related U.S. Application Data

(63) Continuation of application No. 15/069,371, filed on Mar. 14, 2016, now Pat. No. 10,098,964.

(60) Provisional application No. 62/132,219, filed on Mar. 12, 2015.

(51) Int. Cl.

| | | |
|---|---|---|
| *A61K 47/69* | (2017.01) | |
| *A61K 31/225* | (2006.01) | |
| *A23L 33/00* | (2016.01) | |
| *A23L 33/10* | (2016.01) | |
| *A23L 33/15* | (2016.01) | |
| *A23L 33/16* | (2016.01) | |
| *A23L 33/155* | (2016.01) | |
| *A23L 33/17* | (2016.01) | |
| *A61K 31/07* | (2006.01) | |
| *A61K 31/355* | (2006.01) | |
| *A61K 31/25* | (2006.01) | |
| *A23L 33/12* | (2016.01) | |
| *A61K 31/593* | (2006.01) | |
| *A61K 45/06* | (2006.01) | |

(52) U.S. Cl.
CPC ......... *A61K 47/6949* (2017.08); *A23L 33/10* (2016.08); *A23L 33/12* (2016.08); *A23L 33/15* (2016.08); *A23L 33/155* (2016.08); *A23L 33/16* (2016.08); *A23L 33/17* (2016.08); *A23L 33/40* (2016.08); *A61K 31/07* (2013.01); *A61K 31/225* (2013.01); *A61K 31/25* (2013.01); *A61K 31/355* (2013.01); *A61K 31/593* (2013.01); *A61K 45/06* (2013.01); *A61K 47/6951* (2017.08); *A23V 2002/00* (2013.01)

(58) Field of Classification Search
CPC ............ A61K 47/6949; A61K 47/6951; A61K 31/225; A23L 33/155; A23L 33/15; A23L 33/10; A23L 33/16; A23L 33/17; A23L 33/40; A23V 2002/00

USPC .......................................................... 514/58
See application file for complete search history.

(56) References Cited

U.S. PATENT DOCUMENTS

| | | | |
|---|---|---|---|
| 6,217,915 B1 | 4/2001 | Luchansky et al. | |
| 6,767,557 B2 | 7/2004 | Ulrich et al. | |
| 10,098,964 B2 * | 10/2018 | Donovan | A61K 47/6951 |
| 2006/0217441 A1 | 9/2006 | Akimoto et al. | |

FOREIGN PATENT DOCUMENTS

| | | |
|---|---|---|
| EP | 0346006 A1 | 12/1989 |
| WO | 2005077336 A1 | 8/2005 |

OTHER PUBLICATIONS

Velasco et al. Variables affecting lipid oxidation in dried microencapsulated oils. Grasas y Aceites vol. 54. No. 3 (2003), 304-314. (Year: 2003).*
Astray et al., "A Review on the Use of Cyclodextrins in Foods," Food Hydrocolloids, 23(7):1631-1640, Oct. 2009.
Bhandar et al., "Lemon Oil to β-Cyclodextrin Ratio Effect on the Inclusion Efficiency of β-Cyclodextrin and the Retention of Oil Volatiles in the Complex," J. Agric. Food Chem., 46(4):1494-1499, Mar. 1998.
Cabral Marques, H., "A Review on Cyclodextrin Encapsulation of Essential Oils and Volatiles," Flavour and Fragrance Journal, 25(5):313-326, Sep. 2010.
Gaschott et al., "Tributyrin, a Stable and Rapidly Absorbed Prodrug of Butyric Acid, Enhances Antiproliferative Effects of Dihydroxycholecalciferol in Human Colon Cancer Cells," J Nutr., 131(6):1839-1843, Jun. 2001.
Gibbs et al., "Encapsulation in the Food Industry: A Review," Int J Food Sci Nutr., 50(3):213-224, May 1999.
Hedges, A.R., "Industrial Applications of Cyclodextrins," Chem Rev., 98(5):2035-2044, Jul. 1998.

(Continued)

*Primary Examiner* — Yih-Horng Shiao
(74) *Attorney, Agent, or Firm* — Haukaas Fortius PLLC; Michael H. Haukaas

(57) ABSTRACT

The invention provides novel formulations comprising a stable inclusion complex of tributyrin and a cyclodextrin. In one particular embodiment, the formulation comprises an oven dried inclusion complex of tributyrin and γ-cyclodextrin that is effective in minimizing or preventing the unpleasant taste and odor of tributyrin, thus making it suitable for oral administration and delivery to the digestive tract and intestines. The invention provides compositions of these inclusion complexes and methods of using them that are advantageous as food, medicinal and other products, where the negative sensory properties of tributyrin can be a liability.

17 Claims, 4 Drawing Sheets

(56) References Cited

OTHER PUBLICATIONS

Ibekwe et al., "An Investigation into the in Vivo Performance Variability of pH Responsive Polymers for Ileo-Colonic Drug Delivery Using Gamma Scintigraphy in Humans," J Pharm Sci., 95(12):2760-2766, Dec. 2006.
Kang et al., "Dual Function of Tributyrin Emulsion: Solubilization and Enhancement of Anticancer Effect of Celecoxib," Int J Pharm., 428(1-2):76-81, May 2012.
Lee et al., "Stability Characterization and Sensory Testing in Food Products Containing Microencapsulants," Microencapsulation in the Food Industry, Dec. 2014, pp. 367-381.
Leonel et al., "Butyrate: Implications for Intestinal Function," Curr Opin Clin Nutr Metab Care., 15(5):474-479, Sep. 2012.
Li et al., "Emulsion-Based Delivery Systems for Tributyrin, a Potenail Colon Cancer Preventative Agent," J Agric Food Chem., 57(19):9243-9249, Oct. 2009.
Martin Del Valle, E.M., "Cyclodextrins and Their Uses: A Review," Process BioChem., 39(9):1033-1046, May 2004.
Regiert et al, "Application of Y-Cyclodextrin for the Stabilization and/or Dispersion of Vegetable Oils Containing Triglycerides of Polyunsaturated Acids," J Incl Phenom Macrocycl Chem., 25:213-216, Mar. 1996.
Reineccius et al., "Encapsulation of Flavors Using Cyclodextrins: Comparison of Flavor Retention in Alpha, Beta, and Gamma Types," J. Food Sci., 67(9):3271-3279, Jul. 2006.
Roda et al., "A New Oral Formulation for the Release of Sodium Butyrate in the Ileo-Cecal Region and Colon," World J Gastroenterol., 13(7):1079-1084, Feb. 2007.
Sobel et al., "Introduction to Microencapsulation and Controlled Delivery in Foods," Microencapsulation in the Food Industry, Jan. 2014, pp. 3-12.
Szejtli et al., "Elimination of Bitter, Disgusting Tastes of Drugs and Foods by Cyclodextrins," Eur J Pharm Biopharm., 61(3):115-125, Oct. 2005.
Szejtli et al., "Inclusion Complexes of Unsaturated Fatty Acids with Amylose and Cyclodextrin," Die Starke, 27(11):368-376, Jan. 1975.
Szente et al., "Cyclodextrins as Food Ingredients," Trends Food Sci Technol., 15(3):137-142, Mar. 2004.

* cited by examiner

INCLUSION COMPLEXES AND METHODS FOR MAKING THE SAME

RELATED APPLICATIONS

This application is a Continuation of U.S. patent application Ser. No. 15/069,371, filed Mar. 14, 2016, now issued as U.S. Pat. No. 10,098,964, which claims priority under 35 U.S.C. § 119(e) to U.S. Provisional Patent Application No. 62/132,219, filed Mar. 12, 2015, which applications are incorporated herein by reference.

GOVERNMENT SUPPORT

This invention was made with government support under Hatch Project Grant No. ILLU-698-380 awarded by the USDA National Institute of Food and Agriculture. The government has certain rights in the invention.

BACKGROUND OF THE INVENTION

Three major short chain fatty acids (SCFA) produced in the human gastrointestinal tract are acetate, propionate, and butyrate. The growth of bacteria, primarily *Bifidobacterium* and *Lactobacillus*, is stimulated by the presence of non-digestible food whose fermentative action produce SCFA's (Wong J M, de Souza R, Kendall C W, Emam A, Jenkins D J, *Colonic health: Fermentation and short chain fatty acids*, J Clin Gastroenterol., 2006; 40 (3):235). Butyrate is responsible for various beneficial health effects, including improvement of the intestinal structure of piglets with short-bowel syndrome (Bartholome A L, Albin D M, Baker D H, Holst J J, Tappenden K A, *Supplementation of total parenteral nutrition with butyrate acutely increases structural aspects of intestinal adaptation after an 80% jejunoileal resection in neonatal piglets*, J of Parenter Enteral Nutr. 2004; 28 (4):210-222), decreasing the proliferation of colon cancer cells in human cell lines (Lupton J R., *Microbial degradation products influence colon cancer risk: The butyrate controversy*, J Nutr., 2004; 134 (2):479-482), decreasing the incidence of diarrhea (Berni Canani R, Terrin G, Cirillo P, et al., *Butyrate as an effective treatment of congenital chloride diarrhea*, Gastroenterol., 2004; 127 (2): 630-634), improvement in inflammatory bowel disease (Scarpellini E, Lauritano E C, Lupascu A, et al., *Efficacy of butyrate in the treatment of diarrhoea-predominant irritable bowel syndrome*, Dig Liver Dis., 2007; 1 (1):19-22) and small intestine health (Kotunia A, Woliński J, Laubitz D, et al., *Effect of sodium butyrate on the small intestine development in neonatal piglets fed [correction of feed] by artificial sow*, J Physiol Pharmacol. 1994; 55 (2):59-68).

Tributyrin is compound that contains, and is a source of, butyric acid; a naturally produced short chain fatty acid related to the maintenance of intestinal health and associated with the improvement of some intestinal disease states. Tributyrin is a triglyceride that contains three moles of butyric acid per mole of tributyrin. Tributyrin is a food additive that is generally regarded as safe (GRAS) (21CFR184.1903) and is a natural component of many dairy items. Tributyrin is rapidly absorbed and chemically stable in plasma where it is converted into butyric acid by intracellular lipases to elicit its beneficial effects (Gaschott T, Steinhilber D, Milovic V, Stein J., *Tributyrin, a stable and rapidly absorbed prodrug of butyric acid, enhances antiproliferative effects of dihydroxycholecalciferol in human colon cancer cells*, Nutr Cancer, 2001; 131 (6):1839-1843). A more immediate release and conversion of tributyrin to butyric acid in the intestinal tract can be achieved with exposure to pancreatic, gastric, or other lipases and esterases (Leonel A J, Alvarez-Leite J I, *Butyrate: Implications for intestinal function*, Curr Opin Clin Nutr Metab Care, 2012; 15 (5):474-479; O'Connor K C, Bailey J E, *Hydrolysis of emulsified tributyrin by porcine pancreatic lipase*, Enzyme Microb Technol., 1988; 10 (6):352-356.). Aside from its conversion to butyrate to elicit beneficial effects, the administration of tributyrin both in-vitro and in-vivo has led to improvement in small intestinal structures (Gaschott, supra), and inhibited growth of colon cancer cell lines (Li Y, Le Maux S, Xiao H, McClements D J, 2009, *Emulsion-based delivery systems for tributyrin, a potential colon cancer preventative agent*, J Agric Food Chem 57 (19):9243-9).

However, tributyrin is associated with negative sensory qualities including high bitterness and aroma attributes, such as vomit-like, fecal, and cheesy. Characterized by unpleasant odor and taste, its use in food as a functional ingredient poses a challenge.

Inflammatory bowel disease (IBD) refers to two chronic diseases that cause inflammation of the intestines: ulcerative colitis and Crohn's disease. Whereas ulcerative colitis is an inflammatory disease of the large intestine that affects the mucosa of the intestine which becomes inflamed and develops ulcers, Crohn's disease most commonly affects the last part of the small intestine, the terminal ileum, and parts of the large intestine. However, Crohn's disease is not limited to these areas and can occur in any part of the digestive tract. Crohn's disease causes inflammation that extends much deeper into the layers of the intestinal wall than ulcerative colitis does. Crohn's disease generally tends to involve the entire bowel wall, whereas ulcerative colitis affects only the lining of the bowel.

Medical research has not determined yet what causes inflammatory bowel disease. It has been postulated that a number of factors may be involved, such as the environment, diet, and possibly genetics. The drug treatment for IBD usually consists of anti-inflammatory drugs and immunosuppressive agents. However, current therapy to control IBD is not always effective, and surgical procedures are necessary in many cases. Today, about 70 to 80% of patients with Crohn's disease and about 30 to 40% with ulcerative colitis ultimately require surgery, indicating the lack of efficiency of the currently used therapeutics.

Colorectal cancer is the second most common cause of new cancer cases and cancer deaths in the United States, with an estimated 146,940 new cases and 56,730 deaths in 2004 (Jemal et al., Cancer Statistics, 2004, *CA: A Cancer Journal for Clinicians*, 54: 8-29). It has been suggested that a significant fraction of colon cancers could be prevented by moderate changes in diet and lifestyle. Epidemiological and experimental studies suggest that dietary fiber is protective against the development of colon cancer, with these effects being mainly attributed to the production of short-chain fatty acids. For many years, butyric acid, an important short-chain fatty acid produced by dietary fiber fermentation in the colon, has been investigated for its potential preventive effects. Butyrate has been reported to inhibit cancer cell proliferation and to stimulate the growth of healthy cells. As well as being produced by microbial fermentation of dietary fiber, butyric acid is also found naturally in vegetable oils and animal fats. Although the potential of butyrate as an antitumor agent has been recognized, its application as a therapeutic agent has been hampered because of difficulties in consistently delivering physiologically efficacious concentrations to the site of action, that is, the colon. The poor clinical response has been suggested to be related to butyrate's rapid metabolism and very short half-life in human plasma (<6 min), which causes inability to reach therapeutically effective serum concentrations.

Currently, butyric acid (butyrate) is used in the treatment of IBD, but the actual delivery of butyric acid into the gastrointestinal tract is problematic. Several mechanisms have already been proposed, including the use of butyrate coated tablets, butyrate enemas or the use of natural fermentation in the gastrointestinal tract using dietary fiber. These currently known approaches show significant drawbacks. When using butyric coated tablets, the problem lies in the release of their content at the intended location and because of the inter-individual differences in gastrointestinal tract lumen pH and transit time (Ibekwe et al., *An investigation into the in vivo performance variability of pH responsive polymers for ileo-colonic drug delivery using gamma scintigraphy in humans*, J Pharm Sci, 2006; 95:2760-6; Roda et al., *A new oral formulation for the release of sodium butyrate in the ileo-cecal region and colon*, World J Gastroenterol, 2007; 13:1079-84, the release cannot be optimized. Moreover, taste and odor of the tablets is very unpleasant despite being encased in a coating. The use of rectal butyric acid enemas on the other hand is hampered by a low compliance rate and a short and discontinuous exposure of the colon mucosa to butyrate (Breuer et al., 1997, *Short chain fatty acid rectal irrigation for left-sided ulcerative colitis: a randomised, placebo controlled trial*, Gut 40 (4):485-91). When using the fermentation of dietary fiber for butyrate production, the use of resistant starch and oligofructose have been associated with a greater butyrate production (Morrison et al., *Butyrate production from oligofructose fermentation by the human faecal flora: what is the contribution of extracellular acetate and lactate?*, Br J Nutr., 2006 September; 96 (3):570-7). The stimulation of butyrate production, however, depends on the presence of bacteria expressing butyryl CoA:acetyl CoA transferase and the regional differences in lactate utilizing, butyrate producing bacteria (Morrison et al., supra). Therefore, this approach is not uniform and the outcome cannot be predicted. For the treatment of dysbacteriosis in animals, a powder form or coated butyric acid administration to the feed is used. This results, however, in similar problems as stated above, additionally having a negative sensory aspect that is unfavorable for the animals.

Tributyrin, a prodrug of buytric acid, is a short-chain fatty acid triglyceride that can overcome the disadvantages of butyric acid. Because it is rapidly absorbed and chemically stable in blood plasma, tributyrin diffuses through biological membranes and is metabolized by intracellular lipases, thereby releasing butyrate in therapeutically effective concentrations over time directly into the cell. Previous attempts to enclose tributyrin in a gel capsule or to mask its taste and smell with a flavorant have not satisfactorily overcome the bitter taste and foul odor characteristics.

Cyclodextrins are cyclic oligosaccharides with hydroxyl groups on the outer surface and a void cavity in the center. Their outer surface is hydrophilic, and therefore they are usually soluble in water, but the cavity has a lipophilic character. The most common cyclodextrins are α-cyclodextrin, β-cyclodextrin and γ-cyclodextrin, consisting of 6, 7 and 8 α-1,4-linked glucose units, respectively. The number of these units determines the size of the cavity. Cyclodextrins are capable of forming inclusion complexes with a wide variety of hydrophobic molecules by taking up a whole molecule, or some part of it, into the cavity. The stability of the complex formed depends on how well the guest molecule fits into the cyclodextrin cavity. Common cyclodextrin derivatives are formed by alkylation (e.g., methyl- and ethyl-β-cyclodextrin) or hydroxyalkylation of the hydroxyl groups (e.g., hydroxypropyl- and hydroxyethyl-derivatives of α-, β-, and γ-cyclodextrin) or by substituting the primary hydroxyl groups with saccharides (e.g., glucosyl- and maltosyl-β-cyclodextrin).

Cyclodextrins as wall materials are cyclic structures containing repeating units of glucopyranose connected by α-(1, 4) linkages. They are approved for food use (Del Valle, *Cyclodextrins and their uses: A review*, Process Biochem., 2004; 39 (9):1033-1046) in the US and many other countries. Cyclodextrins are commonly found in 6 (alpha-cyclodextrin), 7 (beta-cyclodextrin), and 8 (gamma-cyclodextrin) repeating units. Cyclodextrins are linked in such a way that they possess a hydrophilic outside and an inner hydrophobic cavity. Complexes are formed when compounds of interest enter the hydrophobic cavity in an energetically favorable reaction (Astray et al., *A review on the use of cyclodextrins in foods*, Food Hydrocoll, 2009; 23 (7):1631-1640). This inner cavity gives cyclodextrins the ability to serve as microencapsulation substrates for a variety of compounds including pharmaceutical, cosmetic, and food ingredients (Szente L, Szejtli J., *Cyclodextrins as food ingredients*, Trends Food Sci Technol., 2004; 15 (3-4):137-142; Del Valle, supra; Szejtli J, Szente L., *Elimination of bitter, disgusting tastes of drugs and foods by cyclodextrins*, Eur J Pharm Biopharm., 2005; 61 (3):115-125).

Microencapsulation is a processing technique used in the food, pharmaceutical, and personal care industries. Microencapsulation can isolate compounds from environmental stresses, improve handling and transport of ingredients, control release, add ingredient functionality, and mask unwanted odors and tastes (Shahidi F, Han X, 1993, *Encapsulation of food ingredients*, Crit Rev Food Sci Nutr 33 (6):501-47; Gibbs B F, Kermasha S, Inteaz A, Mulligan C N, *Encapsulation in the food industry: A review*, Int J Food Sci and Nutr. 1999; 50 (3):213-224; Desai K G H, Park H J, 2005, *Recent developments in microencapsulation of food ingredients*; Sobel R, Versic R, Gaonkar A G, 2014, *Introduction to microencapsulation and controlled delivery in foods*, In: A. G. Gaonkar, N. Vasisht, A. R. Khare, R. Sobel, editors. *Microencapsulation in the Food Industry*. 1st ed. San Diego, Calif.: Academic Press, pp 3-12). Odor and taste masking using microencapsulation is a popular method utilized for functional ingredients with unpleasant sensory qualities, such as iron (Boccio et al., 1997, *A new procedure to fortify fluid milk and dairy products with high-bioavailable ferrous sulfate*, Nutr. Rev. 55 (6):240-6; Xia S, Xu S, 2005, *Ferrous sulfate liposomes: preparation, stability and application in fluid milk*, Food Res Int 38 (3):289-96), polyphenols (Davidov-Pardo et al., 2012, *Sensory and consumer perception of the addition of grape seed extracts in cookies*, J Food Sci 77 (12):S430-8.), ginseng (Tamamoto L C, Schmidt S J, Lee S, 2010, *Sensory properties of ginseng solutions modified by masking agents*, J Food Sci 75 (7): S341-7), fish oils (Serfert Y, Drusch S, Schwarz K, 2010, *Sensory odour profiling and lipid oxidation status of fish oil and microencapsulated fish oil*, Food Chem., 123 (4):968-75.), and other food products (Del Valle, supra; Szente and Szejtli, supra; Szejtli and Szente, supra).

Microencapsulation involves the incorporation of food ingredients, enzymes, or other materials in surrounding matrices to enhance their stability, target intestinal delivery, or to mask odors and taste (Gharsallaoui A, Roudaut G, Chambin O, Voilley A, Saurel R., *Applications of spray drying in microencapsulation of food ingredients: An overview*, Food Res Int. 2007; 40:1107). Microencapsulation can be accomplished by physical and chemical means. Physical means include spray drying, spray chilling, spray coating and extrusion, while chemical methods often include cyclodextrin inclusion or liposome entrapment (Gibbs et. al., supra).

Microencapsulation methods differ in the mechanism that they mask or eliminate the unpleasant sensory qualities of functional ingredients. Techniques such as spray drying, can provide a physical barrier of the core to the system in order to reduce taste and odor perception (Shahidi, supra; Gharsallaoui, supra). Other encapsulation methods, such as complexation with cyclodextrins (CDs), can mask the taste and odor of a core through chemical interactions by trapping the core compound within the CD cavity. This chemical complexation can limit or completely inhibit the cores ability to interact with sensory receptors, thereby reducing or eliminating the sensory perception of the core ingredient (Hedges, A R, *Industrial Applications of Cyclodextrins*, Chem. Rev., 1998, 98:2035-2044; Szejtli and Szente, supra).

It has been observed that microencapsulation has the ability to change the sensory profile of the encapsulated core ingredient (Galmarini et al., 2008, *Aromatic profiles of spray-dried encapsulated orange flavours: influence of matrix composition on the aroma retention evaluated by sensory analysis and electronic nose techniques*, Int J Food Sci Tech 43 (9):1569-76). As a result, the microencapsulated ingredient may not possess the same sensory quality as it did prior to microencapsulation. When included into foods, significant flavor-binding interactions involving wall materials and food components can further modulate the sensory properties of the encapsulated ingredient (Jasinski, E M and Kilara, A, 1985, *Flavor binding properties of whey proteins*, Milchwissenschaft, 40 (7): 596-599; Plug H, Haring G, 1994, *The influence of flavour-ingredient interactions on flavour perception*, Food Qual Prefer, 5, 95-102; O'Neill T E, 1996, *Flavor binding by food proteins: An overview*, in: McGorrin R J, Leland J V, eds., Flavor-Food Interactions, Ch. 6, pp 59-74, Washington, D.C.: American Chemical Society; Hansen, A P and Booker, D C, 1996, *Flavor Interaction with Casein and Whey Protein*, in: McGorrin R J, Leland J V, eds., Flavor-Food Interactions, Ch. 7 pp 75-89, Washington, D.C.: American Chemical Society). Therefore, the knowledge of how a microencapsulated system behaves when included in food and its effect on the sensory properties of the food system as a whole is important for its ultimate utilization in consumer goods.

In order to assess the sensory impact a microencapsulated ingredient has on a food matrix, a variety of sensory testing methodologies, including discrimination tests, can be utilized (Stone, H, Bleibaum, R, Thomas, H A, 2012, *Sensory Evaluation Practices,* $4^{th}$ ed., Elsevier Science). Using the rating method, R-index measures can be calculated (Brown J, 1974, *Recognition assessed by rating and ranking*, Br J Psychol 65 (1):13-22) from panelist judgments to determine if a sample containing a known signal, or variable, varies from a noise, or control (O'Mahony M, 1992, *Understanding discrimination tests: a user-friendly treatment of response bias, rating and ranking R-index tests and their relationship to signal detection*, J Sens Stud 7 (1):1-47). R-index measures convey the probability that a participant will notice a difference relative to the control (O'Mahony, supra). The testing methodology is beneficial over traditional discrimination methods for several reasons: 1) multiple comparisons to a single noise can be made, decreasing the amount of tasting overall for samples that are fatiguing and/or available in limited quantities; 2) R-index accounts for response bias, a common psychological error associated with some types of difference testing; 3) R-index measures give quantitative values of the degree of difference related to the control, and not just if overall differences exist (O'Mahony, supra; Lee H S, van Hout D, 2009, *Quantification of sensory and food quality: The R-index analysis*, J Food Sci 74 (6):R57-64)). These measures have been used in pervious literature to observe differences in functional energy drinks (Tamamoto, supra), inulin included milk beverages (Villegas et al., 2007, *Inulin Milk Beverages: Sensory Differences in Thickness and Creaminess Using R-Index Analysis of the Ranking Data*, Journal of Sensory Studies, 22: 377-393), sugar-based products (Urbanus et al., *Sensory differences between product matrices made with beet and cane sugar sources*, J Food Sci. 2014 November; 79 (11): S2354-61), and guava beverages (Argaiz et al., 2005, *Sensory Detection of Cooked Flavor Development during Pasteurization of a Guava Beverage Using R-index*, Journal of Food Science, 70: S149-S152).

Many humans take a nutritional formula on a regular basis to treat or prevent a nutritional deficiency. The formulas typically contain a balance of proteins, carbohydrates, lipids, vitamins, and minerals tailored to the nutritional needs of the intended user and include product forms such as ready-to-drink liquids, reconstitutable powders, nutritional bars, and the like. Among the many different kinds of nutritional formulas commercially available today, infant formulas have become particularly well known and commonly used in providing a supplemental, primary, or sole source of nutrition early in life.

Due to the importance of taste in consumer acceptance (Moskowitz H R, Kreiger B, 1993, *What sensory characteristics drive product quality? An assessment of individual differences*, J Sens Stud 8 (4):271-82), the negative odor and taste qualities, along with the solubility issues associated with tributyrin and butyric acid limit its use in food. Despite the advantageous properties of tributyrin described above, direct oral administration has not been feasible because of tributyrin's extremely bitter taste and disagreeable odor (vomit-like, fecal). Accordingly, there is a need for a tributyrin composition with improved sensory properties. More particularly, there is a need for a tributyrin composition that can be orally administered while minimizing or preventing its bitter taste and disagreeable odor. There is also a need for a tributyrin composition that can be delivered to the digestive tract and intestines.

SUMMARY

The invention provides new formulations comprising tributyrin and a cyclodextrin. The invention is, inter alia, based on the discovery that formulations comprising tributyrin are gustatorily and olfactorily neutral when formulated using γ-cyclodextrin. Through microencapsulation and oven drying, we have produced a stable complex of tributyrin and γ-cyclodextrin that is indistinguishable from a control sample that did not contain tributyrin when tasted by consumers. The invention is useful as a food product without conferring negative sensory properties as a potential functional food ingredient. The invention can also be used in other products where the negative sensory properties of tributyrin can be a liability, such as in medicinal treatment for intestinal diseases and disorders.

In certain embodiments, the invention provides a stable inclusion complex comprising tributyrin and a cyclodextrin. In embodiments, the cyclodextrin is one or more of α, β, or γ-cyclodextrin. In some embodiments, the cyclodextrin is γ-cyclodextrin. In particular embodiments, the inclusion complex comprising tributyrin and a cyclodextrin can have a molar ratio of tributyrin to γ-cyclodextrin of about 1:1, or greater than or equal to about 1:1. In certain embodiments, the molar ratio can be about 1:0.5 to about 1:20, about 1:1 to about 1:10, or about 1:1 to about 1:3.

The invention provides the unexpected finding that inclusion complexes of tributyrin and γ-cyclodextrin are effective in masking the unpleasant odor of tributyrin, thus making the inclusion complexes effective for oral administration and delivery to the small and/or large intestines.

In other embodiments, the invention provides an administration formulation comprising an inclusion complex of the present disclosure together with suitable pharmaceutical auxiliaries.

In embodiments, the invention additionally provides a method of treating or preventing a condition treatable or preventable with tributyrin, comprising administering to a subject in need of such treatment or prevention a pharmaceutically acceptable effective amount of a stable inclusion complex comprising tributyrin and a cyclodextrin.

In continuity with the present disclosure, a method for preparing a stable inclusion complex of tributyrin and a cyclodextrin is provided, comprising: mixing the cyclodextrin with water to form a first mixture; adding tributyrin to the first mixture to form a second mixture; mixing the second mixture to form a first inclusion complex; centrifuging the first inclusion complex and decanting it to provide a centrifugate; and drying the centrifugate and crushing (grinding or pulverizing) it to form a powdered stable inclusion complex of tributyrin and a cyclodextrin.

In embodiments, a method for preparing a stable inclusion complex of tributyrin and a cyclodextrin is provided, the method comprising: shear mixing a cyclodextrin with water for about 1 minute at about 8,000 rpm to form a first mixture; to the first mixture, adding tributyrin to form a second mixture; shear mixing the second mixture for about 20 minutes at about 8,000 rpm to form a first inclusion complex; allowing the first inclusion complex to sit at room temperature for about 6 hours, followed by shear mixing for at least 1 minute to form a second inclusion complex; allowing the second inclusion complex sit at room temperature for about 20 hours, wherein excess tributyrin and water is removed from the second inclusion complex by decanting, thereby forming a third inclusion complex; centrifuging the third inclusion complex for about 15 minutes at about 3,000 rpm, followed by decanting excess tributyrin and water to form a fourth inclusion complex; placing the fourth inclusion complex on a glass surface and heating for at least 3 hours at about 45° C. to form a solid inclusion complex having from about 9% to about 11% by weight water content; and grinding (crushing or pulverizing) the solid inclusion complex to form a powdered stable inclusion complex.

In embodiments, the invention provides a formula suitable for feeding an infant comprising administering a therapeutically effective amount of the inclusion complex described herein to an infant in need of such treatment.

In embodiments, the invention provides a method of treating inflammatory bowel disease comprising administering a therapeutically effective amount of the inclusion complex described herein to a mammal in need of such treatment.

In embodiments, the invention provides a method of prophylactically protecting against the onset of inflammatory bowel disease comprising administering a prophylactically effective amount of the inclusion complex described herein to a mammal desiring prophylactic protection against the onset of inflammatory bowel disease.

The foregoing and other objects and features of the disclosure will become more apparent from the following detailed description, which proceeds with reference to the accompanying figures. Further embodiments, forms, features, aspects, benefits, objects, and advantages of the invention shall become apparent from the detailed description and figures provided herewith.

DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
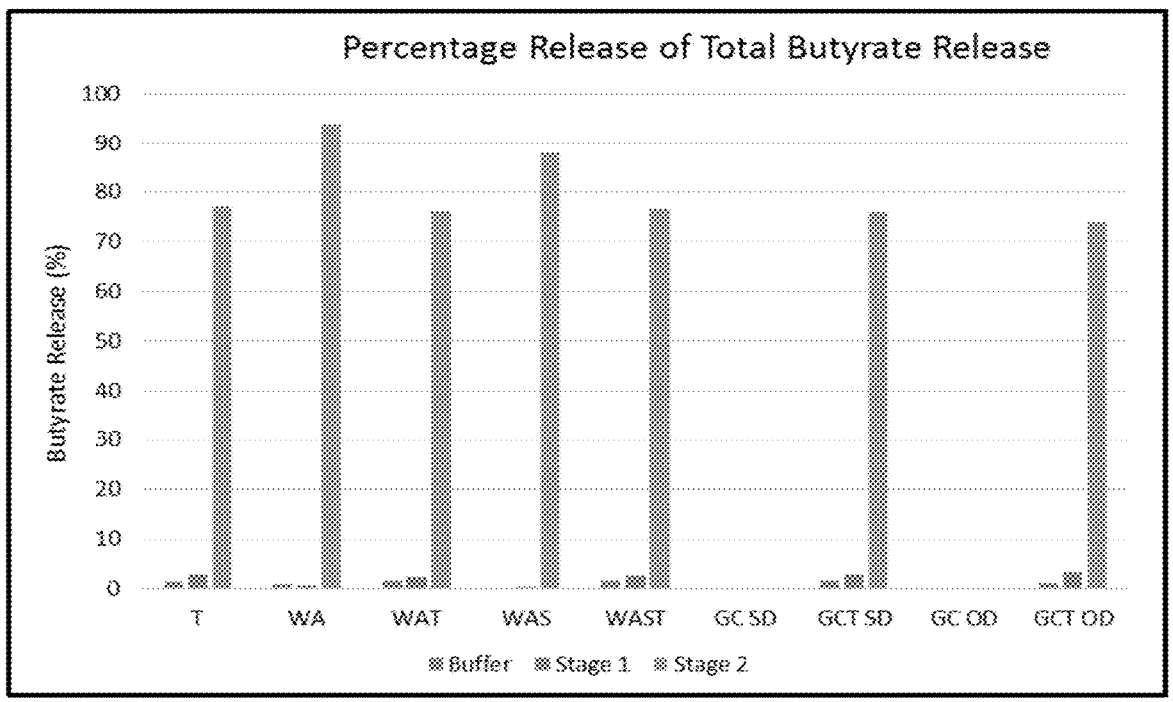
FIG. 1: Percentage Release of Total Butyrate Release.

The present disclosure provides compositions that are microencapsulated preparations of a compound known as tributyrin. Microencapsulation is a processing technique wherein one or more compounds are surrounded, encapsulated or entrapped by one or more compounds. In certain embodiments, tributyrin can be microencapsulated in a compound known as gamma (γ)-cyclodextrin and oven dried to form a stable inclusion complex that is food safe. By stable, we mean the inclusion complex will not degrade, or be contaminated, damaged, disrupted or compromised, so that it can be prepared, stored and applied for its end use, while minimizing or preventing the negative sensory characteristics of tributyrin from being significantly noticed by a subject to which it was administered. Stated otherwise, the preparation, storage and application of the inclusion complex will provide a composition that has the ability to minimize or prevent the bitter taste and foul odor of tributyrin, and this ability will remain steadfast. The stable inclusion complex can be formulated into a flavorless and odorless powder or capsule that is suitable for oral administration in food and medicinal products.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", "in embodiments", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular terms "a," "an," and "the" include plural reference unless the context clearly indicates otherwise. Similarly, the word "or" is intended to include "and" unless the context clearly indicates otherwise.

As used herein, "comprising" is synonymous with "including," "containing," or "characterized by," and is inclusive or open-ended and does not exclude additional, unrecited elements or method steps. Hence, "comprising A or B" means "including A" or "including B" or "including A and B."

As used herein, "consisting of" excludes any element, step, or ingredient not specified in the aspect element.

As used herein, "consisting essentially of" does not exclude materials or steps that do not materially affect the basic and novel characteristics of the aspect.

In each instance herein any of the terms "comprising", "consisting essentially of" and "consisting of" may be replaced with either of the other two terms. The disclosure illustratively described herein suitably may be practiced in the absence of any element or elements, limitation or limitations which are not specifically disclosed herein.

It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrase "one or more" or "at least one" is readily understood by one of skill in the art, particularly when read in context of its usage.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

When a group of substituents is disclosed herein, it is understood that all individual members of that group and all subgroups, including any isomers, enantiomers, and diastereomers of the group members, are disclosed separately. When a compound is described herein such that a particular isomer, enantiomer or diastereomer of the compound is not specified, for example, in a formula or in a chemical name, that description is intended to include each isomer and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

When molecules disclosed herein contain one or more ionizable groups [groups from which a proton can be removed (e.g., —COOH) or added (e.g., amines) or which can be quaternized (e.g., amines)], all possible ionic forms of such molecules and salts thereof are intended to be included individually in the disclosure herein. With regard to salts of the compounds herein, one of ordinary skill in the art can select from among a wide variety of available counterions that are appropriate for preparation of salts of this disclosure for a given application. In specific applications, the selection of a given anion or cation for preparation of a salt may result in increased or decreased solubility of that salt.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

The term "infant" as used herein, unless otherwise specified, refers to children not more than about one year of age, and includes infants from 0 to about 4 months of age, infants from about 4 to about 8 months of age, infants from about 8 to about 12 months of age, low birth weight infants at less than 2,500 grams at birth, and preterm infants born at less than about 37 weeks gestational age, typically from about 26 weeks to about 34 weeks gestational age.

The term "child" or "children" as used herein refers to children not more than 12 years of age and includes children from about 12 months to about 12 years of age. The term "adult" as used herein refers to adults and children about 12 years and older.

The term "base nutritional powder" as used herein, unless otherwise specified, refers to a powdered nutritional composition that has been subjected to a drying process but does not include any dry blended components and is designed for infants, toddlers, children adults, or combinations thereof, that contains nutrients such as proteins, carbohydrates, lipids, vitamins, minerals, and electrolytes to potentially serve as a supplement, primary, or sole source of nutrition.

The term "nutritional powder" as used herein, unless otherwise specified, refers to a powdered nutritional composition that has been subjected to a drying process and includes dry blended ingredients and is designed for infants, toddlers, children adults, or combinations thereof, that contains sufficient nutrients such as proteins, carbohydrates, lipids, vitamins, minerals, and electrolytes to potentially serve as a supplement, primary, or sole source of nutrition.

The term "infant formula" as used herein, unless otherwise specified, refers to a nutritional composition designed for infants that contains sufficient nutrients such as proteins, carbohydrates, lipids, vitamins, and minerals to potentially serve as a supplemental, primary, or sole source of nutrition.

The term "dry blended" as used herein, unless otherwise specified, refers to the addition of a component or ingredient into a base nutritional powder.

As used herein, the term "tributyrin", also known as glyceryl tributyrate or tributyl glycerol or 1,3-di(butanoyloxy)propan-2-yl butanoate ($C_{15}H_{26}O_6$) has a molecular weight of 302.36 g/mol. Tributyrin can be prepared synthetically by the esterfication of glycerol in the presence of excess butyric acid. Tributyrin is readily available in bulk quantities from several national and international suppliers, such as Aldrich, Milwaukee, Wis. Acid and/or enzymatic hydrolysis of tributyrin yields about three molar equivalents of butyric acid.

As used herein, the term "cyclodextrin" can refer to a cyclic dextrin molecule that is formed by enzyme conversion of starch. Cyclodextrins are cyclic oligosaccharides. The most common cyclodextrins are α-cyclodextrin, which is composed of a ring of six glucose residues; β-cyclodextrin, which is composed of a ring of seven glucose residues; and γ-cyclodextrin, which is composed of a ring of eight glucose units. The inside cavity of a cyclodextrin is lipophilic, while the outside of the cyclodextrin is hydrophilic; this combination of properties has led to widespread study of the natural cyclodextrins, particularly in connection with pharmaceuticals, and many inclusion complexes have been reported. β-Cyclodextrin is not known to have any toxic effects, is World-Wide GRAS (i.e., Generally Regarded As Safe) and natural, and is FDA approved. α-Cyclodextrin and γ-cyclodextrin are also considered natural products and are U.S and E.U. GRAS. α-, β- or γ-cyclodextrins prepared by the enzymatic conversion of starch differ in the diameter of their hydrophobic cavity and are generally suitable for inclusion of numerous lipophilic substances.

As used herein, the term "dietary fiber" can refer to the edible parts of plants or analogous carbohydrates that are resistant to digestion and absorption in the human small intestine, with complete or partial fermentation in the large intestine.

The term "delayed release" can refer to a release that is substantially post-gastric.

The term "sustained release" can refer to the total release of the compound or composition, which is slow and sustained over a period of time, as opposed to being released as a bolus.

The term "mammal" is readily understood by one of ordinary skill in the art and can, for example, refer to humans, rats, mice, rodents, guinea pigs, dogs, cats, and primates.

Unless otherwise explained, all technical and scientific terms used herein have the same meaning as commonly understood by one of ordinary skill in the art to which a disclosed disclosure belongs.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art, especially in light of the detailed disclosure provided herein. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

All references (i.e., patents and publications) mentioned in the specification are indicative of the levels of skill of those skilled in the art to which the disclosure pertains. References cited herein are incorporated by reference herein in their entirety, as though individually incorporated by reference, to the extent each reference is at least partially not inconsistent with the disclosure in this application (for example, a reference that is partially inconsistent is incorporated by reference except for the partially inconsistent portion of the reference). The references indicate the state of the art as of their publication or filing date and it is intended that this information can be employed herein, if needed, to exclude specific embodiments that are in the prior art.

In embodiments, the invention provides a rapidly dissolving orally administrable powder comprising: at least one active ingredient comprising calcium; at least one natural flavor; at least one sweetener; at least one disintegrant; at least one organic acid; and an inclusion complex comprising tributyrin and a cyclodextrin. In certain embodiments, the organic acid may be selected from a broad range of organic acids, such as citric acid, malic acid, fumaric acid, tartaric acid, lactic acid, ascorbic acid, oxalic acid, malonic acid, uronic acid, quinic acid, succinic acid, levulinic acid, and mixtures thereof.

A disintegrant is a substance, or a mixture of substances, added to a tablet to facilitate its breakup or disintegration after administration. The active ingredient should be released from the tablet matrix as efficiently as possible to allow for its rapid dissolution. Materials serving as disintegrants have been chemically classified as starches, clays, celluloses, algins, or gums. In embodiments, disintegrants can be corn and potato starch which have been well-dried and powdered. Starch has a great affinity for water and swells when moistened, thus facilitating the rupture of the tablet matrix. However, others have suggested that its disintegrating action in tablets is due to capillary action rather than swelling; the spherical shape of the starch grains increases the porosity of the tablet, thus promoting capillary action. When their disintegration effect is desired, starches are added to the powder blends in the dry state. Starch pastes which are useful as binding agents will generally not be effective as disintegrating agents. Sodium lauryl sulfate in combination with starch also has been demonstrated to be an effective disintegrant. In some cases, the apparent effectiveness of surfactants in improving tablet disintegration has been postulated as being due to an increase in the rate of wetting.

In addition to the starches, a large number of materials have been used and are reported to be effective as disintegrants. This group includes Veegum HV, Ac-Di-Sol, methylcellulose, agar, bentonite, cellulose and wood products, natural sponge, cation-exchange resins (e.g., Amberlite IRP-88), alginic acid, guar gum, citrus pulp, and carboxymethylcellulose. Much research has been reported on disintegrants. For example, see: D. Gissinger and A. Stamm, Drug Develop. Ind. Pharm., 6, 511 (1980), "A Comparative Evaluation of the Properties of Some Tablet Disintegrants"; Rudnic et al., Drug Develop. Ind. Pharm., 7, 347 (1981), "Some Effects of Relatively Low Levels of Eight Tablet Disintegrants on a Direct Compression System"; H. A. Lieberman and L. Lachman, Pharmaceutical Dosage Forms: Tablets, Volume 1, pages 139-140; and R. E. Gordon, The Thermodynamic Characterization of the Solid Surface Interaction for Three Tablet Disintegrating Agents, Ph.D. Thesis, Purdue University, 1981.

In embodiments, inflammatory bowel disease can be treated by administering a therapeutically effective amount of an inclusion complex comprising tributyrin and a cyclodextrin to a mammal in need of such treatment. If needed or recommended, the inclusion complex can be administered daily. In some embodiments, the present disclosure provides a method of treating inflammatory bowel disease comprising administering a therapeutically effective amount of an inclusion complex comprising tributyrin and a cyclodextrin to a mammal in need of such treatment, wherein the inflammatory bowel disease is ulcerative colitis. In other embodiments, the present disclosure provides a method of treating inflammatory bowel disease comprising administering a therapeutically effective amount of an inclusion complex comprising tributyrin and a cyclodextrin to a mammal in need of such treatment, wherein the inflammatory bowel disease is Crohn's disease.

In embodiments, the invention provides a post-gastrically available delayed release oral (DRO) or rectally administrable pharmaceutical composition for the treatment or prophylaxis of inflammatory bowel disease, said composition comprising an inclusion complex of tributyrin and a cyclodextrin as a therapeutically active agent in an amount effective to treat inflammatory bowel disease, together with a pharmaceutically acceptable excipient (e.g., a carrier, vehicle, diluent, disintegrant, etc.).

In embodiments, the invention provides a dietary mixture formulation for special medical purposes, including in combination, the inclusion complex described herein and at least one of the following ingredients: omega-3 fatty acids; Vitamin A; Vitamin D3; Vitamin E in a medium, for the treatment of inflammatory bowel diseases.

In embodiments, considering the sensory performance, digestive stability, and fermentative quality, the inclusion complex described herein is able to provide minimized sensory impact, digestive stability in the stomach with release in the small intestine, and butyrate production throughout all stages of the large intestine. This beneficial finding (helping small and large intestine) targets several populations and addresses the challenge of delivering butyrate to the descending colon.

The majority of the release of the inclusion complex described herein will be targeted to the part of the small intestine or colon where the active disease is prevalent and this varies for Crohn's disease and ulcerative colitis. Thus, typically for an enteric coated capsule, an enteric coating should dissolve in the pH of the jejunum (about pH 5.5), ileum (about pH 6) or colon (about pH 6-7) so as to release the majority of the active from the jejunum to the colon—where most of the active disease is located in IBD. More particularly, in the case of Crohn's disease, most of the active disease is around the terminal ileum and so the enteric coating should dissolve about pH 5.5 to 6. In the case of ulcerative colitis, the disease is mostly in the colon and therefore the enteric coating should dissolve about pH 6 to 7, more particularly about pH 6.8.

Without wishing to be bound by any particular theory, there may be discussion herein of beliefs or understandings of underlying principles or mechanisms relating to embodiments of the disclosure. It is recognized that regardless of the ultimate correctness of any explanation or hypothesis, an embodiment of the disclosure can nonetheless be operative and useful.

Gamma-cyclodextrin is a carbohydrate-based ingredient commonly used in the food, cosmetic, and pharmaceutical industries. Due to the unique circular molecular structure of gamma-cyclodextrin, it is able to surround other molecules through chemical displacement. Gamma-cyclodextrins naturally contain water molecules in the center of their circular structure. Through processing methods, we have shown that water can be displaced with other compounds of interest, particularly, with tributyrin. By surrounding tributyrin in a cyclodextrin inclusion complex, and removing some, most or essentially all of the water, we have protected it from interactions with the environment around the complex. In embodiments, the water level can be less than about 20%, less than about 15%, less than about 10%, less than about 5%, less than about 2% or less than about 1%. The inclusion complex can be formulated into a powder (by grinding, crushing, pulverizing, etc.) suitable for oral administration that results in the protection of the microencapsulated compound from light, pH, temperature, and/or digestion, as well as the reduction or elimination of taste/smell.

In certain embodiments, the present disclosure provides an inclusion complex suitable for use in the preparation of dietary supplements (for example beverages, foods), pills or other similar products suitable for use in regulating the functions of the human body. Dietary fiber includes polysaccharides, oligosaccharides, lignin, and associated plant substances. Dietary fibers promote beneficial physiologic effects, including laxation, blood cholesterol attenuation, and/or blood glucose attenuation. Dietary supplementation with vitamins, minerals, herbs, and other dietary ingredients, together "dietary ingredient", is within the purview of those skilled in the art. These supplements may be used to assist a person in meeting certain dietary needs.

The inclusion complex may take a final form as a flowable granulated or powdered product by itself or admixed with one or more additive ingredients.

Vitamins that may be used in accordance with the present disclosure include, for example: vitamin A from sources such as vitamin A palmitate, vitamin A acetate, beta carotene, combinations thereof, and the like; vitamin C from sources such as sodium ascorbate, ascorbic acid, calcium ascorbate, combinations thereof, and the like; vitamin D from sources such as ergocalciferol ($D_2$), cholecalciferol ($D_3$), combinations thereof, and the like; vitamin E from sources such as d-a-tocopheryl acetate, d-a-tocopherol, d-a-tocopheryl succinate, dl-a-tocopherol, dl-a-tocopheryl succinate, dl-a-tocopheryl acetate, combinations thereof, and the like; thiamin (vitamin $B_1$), thiamin mononitrate, combinations thereof, and the like; riboflavin (vitamin $B_2$), riboflavin 5' monophosphate, combinations thereof, and the like; niacin (vitamin $B_3$) from sources such as niacinamide, nicotinic acid, inositol hexanicotinate, combinations thereof, and the like; vitamin $B_6$ from sources such as pyridoxine hydrochloride, pyridoxal-5'-phosphate, combinations thereof, and the like; folate from sources such as folic acid, folinic acid, combinations thereof, and the like; vitamin $B_{12}$ from sources such as cyanocobalamin, methylcobalamin, combinations thereof, and the like; pantothenic acid (vitamin $B_5$) from sources such as calcium d-pantothenate, pantetheine, pantothenol, sodium pantothenate, combinations thereof, and the like; biotin from sources such as biotin trituration and brewer's yeast, combinations thereof, and the like.

Minerals that may be used in accordance with present disclosure include, for example: calcium from sources such as calcium carbonate, calcium citrate, calcium aspartate, calcium gluconate, calcium lactate, calcium lactate gluconate, calcium citrate malate, dicalcium malate, combinations thereof, and the like; chromium from sources such as chromium polynicotinate, chromium chloride, chromium-enriched yeast, chromium picolinate, chromium amino acid chelate, combinations thereof, and the like; copper from sources such as copper amino acid chelate, copper gluconate, copper sulfate, copper oxide, copper carbonate, combinations thereof, and the like; iodine from sources such as potassium iodide, ammonium iodide, calcium iodide, kelp, combinations thereof, and the like; iron from sources such as iron amino acid chelate, ferrous fumarate, ferrous succinate, ferrous sulfate, ferrous gluconate, ferritin, ferric orthophosphate, combinations thereof, and the like; magnesium from sources such as magnesium oxide, magnesium carbonate, magnesium amino acid chelate; magnesium citrate, magnesium dolomite, magnesium aspartate, magnesium fumarate, magnesium hydroxide, dimagnesium malate, magnesium aspartate, combinations thereof, and the like; manganese from sources such as manganese amino acid chelate, manganese sulfate, manganese gluconate, manganese chloride, combinations thereof, and the like; molybdenum from sources such as sodium molybdate, molybdenum amino acid chelate, combinations thereof, and the like; selenium from sources such as selenium yeast, selenomethionine, sodium selenite, combinations thereof, and the like; zinc from sources such as zinc oxide, zinc gluconate, zinc sulfate, zinc picolinate, zinc amino acid chelate, zinc chloride, combinations thereof, and the like; boron from sources such as boron amino acid complex, sodium borate, combinations thereof, and the like.

Natural flavors that may be used in accordance with the present disclosure include any flavors capable of masking bitter tastes or enhancing sweetness. Natural flavors include, for example: masking flavors, masking powder, bitter masker; sugar flavor, natural flavor cane sugar type, vanilla and cream flavors, chocolate, fruit flavors such as SD natural Saskatoon berry flavor, natural mixed berry flavor, Marion Blackberry WONF, Blueberry WONF, Dark Sweet Cherry WONF, RSP Cherry WONF, Cranberry WONF, Cranberry WONF, Black Currant WONF, Concord Grape WONF, Clear Passionfruit WONF, Cloudy Passionfruit WONF, Peach WONF, Plum WONF, combinations thereof, and the like. Where some flavors, for example vanilla, cream, and/or chocolate flavors are added, an acid such as an organic acid described herein may not be required. In addition, any artificial flavor may be included in the formulation and is within the purview of those skilled in the art, which does not negatively impact the usefulness of the final formulation.

Additional exemplary flavors imparted by a flavoring agent can include a milk flavor, a butter flavor, a cheese flavor, a cream flavor, and a yogurt flavor; a vanilla flavor; tea or coffee flavors, such as a green tea flavor, an oolong tea flavor, a tea flavor, a cocoa flavor, a chocolate flavor, and a coffee flavor; mint flavors, such as a peppermint flavor, a spearmint flavor, and a Japanese mint flavor; spicy flavors, such as an asafetida flavor, an ajowan flavor, an anise flavor, an angelica flavor, a fennel flavor, an allspice flavor, a cinnamon flavor, a chamomile flavor, a mustard flavor, a cardamom flavor, a caraway flavor, a cumin flavor, a clove flavor, a pepper flavor, a coriander flavor, a sassafras flavor, a savory flavor, a Zanthoxyli Fructus flavor, a perilla flavor, a juniper berry flavor, a ginger flavor, a star anise flavor, a horseradish flavor, a thyme flavor, a tarragon flavor, a dill flavor, a capsicum flavor, a nutmeg flavor, a basil flavor, a marjoram flavor, a rosemary flavor, a bayleaf flavor, and a wasabi (Japanese horseradish) flavor; a nut flavor such as an almond flavor, a hazelnut flavor, a macadamia nut flavor, a peanut flavor, a pecan flavor, a pistachio flavor, and a walnut flavor; alcoholic flavors, such as a wine flavor, a whisky flavor, a brandy flavor, a rum flavor, a gin flavor, and a liqueur flavor; floral flavors; and vegetable flavors, such as an onion flavor, a garlic flavor, a cabbage flavor, a carrot flavor, a celery flavor, mushroom flavor, and a tomato flavor.

Nutritional supplements can impact many things, such as growth, weight management, medicinal use, energy, well-being, etc. The inclusion complex disclosed herein are suitable for food supplementation for any purpose including, but not limited to, dietary supplements for infants, the aged, for athletes, for those seeking weight gain, for those recovering from illness or injury. The disclosed inclusion complexes can be provided as tablets, drinks, hot or cold teas, incorporated into bars, or powder formulations.

In embodiments, the invention provides a formula suitable for feeding infants comprising: sugar, non-fat milk, water, an edible fat and an inclusion complex comprising tributyrin and a cyclodextrin. In other embodiments, the present disclosure provides a formula suitable for feeding infants, comprising: protein and/or free amino acids, carbohydrate, water, minerals, vitamins, edible fat and an inclusion complex comprising tributyrin and a cyclodextrin. The inclusion complex can provide a stable liquid infant formula having suitable shelf life. According to one aspect of the present disclosure, a clyclodextrin inclusion complex is provided for incorporation in a formula suitable for feeding infants. The formula comprises a cyclodextrin and tributyrin inclusion complex, sugar, non-fat milk, water and an edible fat, said fat comprising a blend of a vegetable oil and at least one at least one of the following: (a) a fatty acid source of semi-purified or purified origin comprising at least one member of the group of $C_{20}$, $\omega$-6 fatty acids and $C_{22}$, $\omega$-6 fatty acids, wherein the total of said $C_{20}$, $\omega$-6 and said $C_{22}$, $\omega$-6 fatty acids is about 0.13%-5.6% by weight of all fatty acids in the product; and (b) a fatty acid source of semi-purified or purified origin comprising at least one member of the group of $C_{20}$, $\omega$-3 fatty acids and $C_{22}$, $\omega$-3 fatty acids, wherein the total of said $C_{20}$, $\omega$-3 and said $C_{22}$, $\omega$-3 fatty acids is about 0.013-3.33% by weight of all fatty acids in the product. Alternatively, the formula can comprise protein, carbohydrate, water, minerals, vitamins and an edible fat, said fat comprising a blend of egg yolk lipid and an oil selected from the group consisting of coconut oil, soybean oil and mixtures thereof, wherein said egg yolk lipid and oil are present in amounts sufficient to provide an amount of $C_{20}$, $\omega$-6 and $C_{22}$, $\omega$-6 fatty acids of about 5-100 milligrams per 100 milliliters of the formula and an amount of $C_{20}$, $\omega$-3 and $C_{22}$, $\omega$-3 fatty acids of about 0.5-60 milligrams per 100 milliliters of the formula.

Nutraceutical compounds are frequently used to produce supplements capable of providing a person with nutritional components that can improve their performance during physical activity, or of providing substances which would otherwise be lacking due, for example, to an unbalanced slimming diet. In detail, in the former case the supplements currently available on the market are usually based on protein and sugars with appropriate additions of vitamins, usually belonging to groups B, C and E, and/or mineral salts (sodium, potassium, magnesium) so as to obtain a compound capable of delivering a constant and prolonged release of energy, but also of replacing the substances used up during the physical activity. While a cyclodectrin inclusion complex as described herein can be added to the first case in situations where their benefits may be needed, it is more likely the benefits of the inclusion complex will be needed in the latter case. In the latter case, the nutraceutical compounds and thus, the supplements suitable for making up for any deficiencies, due for example to a particular dietary regimen, differ depending on the substances to be integrated. The nutraceutical compounds used in this case are usually characterized by a high protein content to which, for example, the following may be added, depending on the specific requirements: a cyclodextrin inclusion complex as described herein, ginseng, royal jelly, blueberry; or a cyclodextrin inclusion complex as described herein, ginseng, guarana and freeze-dried royal jelly.

Aspects

1. A product comprising any feature described, either individually or in combination with any feature, in any configuration.
2. A method comprising any method described, in any order using any modality.
3. The invention substantially as disclosed herein.
4. An inclusion complex comprising tributyrin and a cyclodextrin.
5. The inclusion complex in aspect 4 wherein the cyclodextrin is γ-cyclodextrin.
6. The inclusion complex in aspect 5 wherein the molar ratio of tributyrin to γ-cyclodextrin is greater than or equal to 1:1.
7. The inclusion complex in aspect 6 wherein the molar ratio of tributyrin to γ-cyclodextrin is from 1:1 to 1:3.
8. An administration formulation comprising an inclusion complex according to aspect 4 together with suitable pharmaceutical auxiliaries.
9. A method of treating or preventing a condition treatable or preventable with a tributyrin, which comprises administering to a subject in need of treatment or prevention a pharmaceutically acceptable administration form according to aspect 7 comprising an effective amount of the tributyrin inclusion complex.
10. A method for preparing a cyclodextrin inclusion complex, comprising:
    a. mixing cyclodextrin with water to form a first mixture;
    b. adding tributyrin to the first mixture to form a second mixture;
    c. mixing the second mixture to form a first inclusion complex;
    d. centrifuging the first inclusion complex and decanting to provide a centrifugate; and
    e. drying the centrifugate and crushing to form a powdered cyclodextrin inclusion complex.
11. A method for preparing a cyclodextrin inclusion complex, the method comprising:
    a. shear mixing γ-cyclodextrin with water for 1 minute at 8,000 rpm to form a first mixture;
    b. to the first mixture, adding tributyrin to form a second mixture;
    c. shear mixing the second mixture for 20 minutes at 8,000 rpm to form a first inclusion complex;
    d. allowing the first inclusion complex to sit at room temperature for 6 hours followed by shear mixing for at least 1 minute to form a second inclusion complex;
    e. allowing the second inclusion complex sit at room temperature for 20 hours wherein excess tributyrin and water is removed from the second inclusion complex by decanting thereby forming a third inclusion complex;
    f. centrifuging the third inclusion complex for 15 minutes at 3,000 rpm followed by decanting excess tributyrin and water to form a fourth inclusion complex;
    g. placing the fourth inclusion complex on a glass surface and heating for at least 3 hours at 45° C. to form a solid inclusion complex having from 9% to 11% by weight water content; and
    h. grinding the solid inclusion complex to form a powdered inclusion complex.

12. A formula suitable for feeding infants comprising: sugar, non-fat milk, water, edible fat and the inclusion complex of aspect 4, 5, 6, or 7.
13. A formula suitable for feeding infants, comprising: protein, carbohydrate, water, minerals, vitamins, edible fat and the inclusion complex of aspect 4, 5, 6, or 7.
14. A rapidly dissolving orally administrable powder comprising:
    a. at least one active ingredient comprising calcium;
    b. at least one natural flavor;
    c. at least one sweetener;
    d. at least one disintegrant;
    e. at least one organic acid; and
    f. the inclusion complex of aspect 4, 5, 6, or 7.
15. A method of treating inflammatory bowel disease comprising administering a therapeutically effective amount of the inclusion complex in aspect 4, 5, 6, or 7 to a mammal in need of such treatment.
16. A method of prophylactically protecting against the onset of inflammatory bowel disease comprising administering a prophylactically effective amount of inclusion complex in aspect 4, 5, 6, or 7 to a mammal desiring prophylactic protection against the onset of inflammatory bowel disease.
17. The method of aspects 15 or 16 wherein the inclusion complex is administered daily.
18. The method of aspects 15 or 16 wherein the inflammatory bowel disease is ulcerative colitis.
19. The method of aspects 15 or 16 wherein the inflammatory bowel disease is Crohn's disease.
20. A post-gastrically available delayed release oral (DRO) pharmaceutical composition for the treatment or prophylaxis of inflammatory bowel disease, said composition comprising the inclusion complex of aspect 4, 5, 6, or 7 as a therapeutically active agent in an amount effective to treat inflammatory bowel disease, together with a pharmaceutically acceptable carrier or vehicle.
21. A dietary mixture formulation for special medical purposes, including in combination the inclusion complex of aspect 4, 5, 6, or 7 and at least one of the following ingredients: omega-3 fatty acids; Vitamin A; Vitamin D3; Vitamin E in a medium, for the treatment of inflammatory bowel diseases.
22. A method of treating colon cancer comprising administering a therapeutically effective amount of the inclusion complex in aspect 4, 5, 6, or 7 to a mammal in need of such treatment.
23. A method of prophylactically protecting against the onset of colon cancer comprising administering a prophylactically effective amount of inclusion complex in aspect 4, 5, 6, or 7 to a mammal desiring prophylactic protection against the onset of colon cancer.
24. The method of aspects 22 or 23 wherein the inclusion complex is administered daily.

While the present disclosure can take many different forms, for the purpose of promoting an understanding of the principles of the disclosure, reference will now be made to the embodiments illustrated in the examples and figures, and specific language will be used to describe the same. It will nevertheless be understood that no limitation of the scope of the disclosure is thereby intended. Any alterations and further modifications of the described embodiments, and any further applications of the principles of the disclosure as described herein are contemplated as would normally occur to one skilled in the art to which the disclosure relates. Every formulation or combination of components described or exemplified herein can be used to practice the disclosure, unless otherwise stated.

For instance, the examples below show that through microencapsulation and oven drying, we have produced a stable inclusion complex of tributyrin and γ-cyclodextrin that is indistinguishable from a control sample that does not contain tributyrin when tasted by consumers. We contemplate that any modification of the exemplified methods that produce a stable inclusion complex of tributyrin and a cyclodextrin will achieve the improved properties exhibited by the exemplified oven dried inclusion complex of tributyrin and γ-cyclodextrin. Accordingly, a skilled artisan can dry the formulation outside of an oven so long as it produces a stable inclusion complex. Similarly, a skilled artisan can interchange α-cyclodextrin or β-cyclodextrin for γ-cyclodextrin so long as it produces a stable inclusion complex. Furthermore, a skilled artisan can utilize a process other than microencapsulation so long as it produces a stable inclusion complex. Finally, a skilled artisan could modify the exemplified spray drying formulation to produce a stable inclusion complex.

The specific embodiments provided herein are examples of useful embodiments of the present disclosure and it will be apparent to one skilled in the art that the present disclosure may be carried out using a large number of variations of the devices, device components, methods and steps set forth in the present description. As will be obvious to one of skill in the art, methods and devices useful for the present methods can include a large number of optional composition and processing elements and steps.

One of ordinary skill in the art will appreciate that starting materials, biological materials, reagents, synthetic methods, purification methods, analytical methods, assay methods, and biological methods other than those specifically exemplified can be employed in the practice of the disclosure without resort to undue experimentation. All art-known functional equivalents, of any such materials and methods are intended to be included in this disclosure. The terms and expressions that have been employed are used as terms of description and not of limitation, and there is no intention that in the use of such terms and expressions of excluding any equivalents of the features shown and described or portions thereof, but it is recognized that various modifications are possible within the scope of the disclosure. Thus, it should be understood that although the present disclosure has been specifically disclosed by exemplary embodiments and optional features, modification and variation of the concepts herein disclosed may be resorted to by those skilled in the art, and that such modifications and variations are considered to be within the scope of this disclosure as defined by the claims.

The spirit and scope of the appended aspects should not be limited, therefore, to the description of the exemplary embodiments contained herein. All embodiments that come within the meaning of the aspects, either literally or by equivalence, are intended to be embraced therein. Furthermore, the advantages described above are not necessarily the only advantages of the disclosure, and it is not necessarily expected that all of the described advantages will be achieved with every embodiment of the disclosure.

EXAMPLES

Example 1: Tibutyrin Retention of GCT OD vs. GCT SD

Cyclodextrins were investigated as encapsulated wall materials utilizing two preparation methods: spray drying and oven drying. Spray drying is a commonly used method of processing in the food industry to cost effectively convert liquid formulations into powdered products (Gharsallaoui A, et. al., supra). Oven drying is a method commonly used in the food industry to dry food products using circulated heat in an enclosed space. As shown in Table 1, spray drying and oven drying yielded markedly different retention results. Spray drying only retained roughly 62% of the tributyrin included into the formulation, however, the same formulation when oven dried retained roughly 85% of the tributyrin. The poor performance of the spray drying may have less to do with the ability of cyclodextrins to encapsulate tributyrin, and rather, more to do with the particular formulation (e.g., solids content, viscosity, etc.) and/or conditions (e.g., drying temperature, pressure, etc.) used in the process. It may also have to do with damage incurred by the complex during prolonged exposure to heat within the spray dryer causing ineffective atomization. It is contemplated that a skilled artisan through appropriate modifications to the formulation, process parameters and/or apparatus, would be able to successfully improve the performance.

TABLE 1

Retention of tributyrin in various microcapsule formulations

| Formulation | Drying Method | Average Retention |
| --- | --- | --- |
| Gamma Cyclodextrin, Tributyrin | Spray Drying | 62.6 ± 2.9% |
| Gamma Cyclodexrin, Tributyrin | Oven Drying | 84.9 ± 5.5% |

Example 2: R-Index Ranking of GCT OD vs. GCT SD

While retention percentages were acceptable for oven dried cyclodextrins, the ultimate goal of this research mainly involved the reduction of the poor sensory qualities associated with tributyrin. For this reason spray dried and oven dried cyclodextrin microencapsulated tributyrin were included in a sensory difference test. The test used was the R-Index by ranking method to determine if the inclusion of the mentioned microencapsulated particles affected the sensory perception of an infant formula. The panel that ranked the samples included 33 total males and females recruited from the University of Illinois campus. In this test, panelists were presented with a sample labeled as a "noise", which served as a control and did not contain any microencapsulates or free tributyrin. It is the infant formula as prepared according to instructions on the label, packaging or insert of the product. The panelists are presented with a coded sample and asked to indicate if the sample is the "noise" or a "signal". A "signal" sample is anything that is perceivable different (in regards to aroma, taste, appearance, or texture) than the "noise". Panelists examined infant formulas containing the same content of tributyrin (microencapsulated or free) to an infant formula containing no tributyrin (noise). Results from the test are shown in Table 2 below.

TABLE 2

R-Index and d' (degree of difference) for various microcapsule formulations in infant formula

| Additive | Average R-Index | Estimated d' value |
| --- | --- | --- |
| Tributyrin (not encapsulated) | 80.5[A] | 1.24 |
| Gamma Cyclodextrin, Tributyrin Spray Dried (GCT SD) | 70.9[A] | 0.78 |
| Gamma Cyclodextrin, Tributyrin Oven Dried (GCT OD) | 49.5[B] | 0 |

[A] denotes significance. Values that share the same letter are not significantly different at an alpha of 0.05

[B] denotes significance. GCT OD is the only sample that has a B superscript. It is significantly different from the other two samples at an alpha of 0.05. This means that samples of unencapsulated tributyrin and GCT SD are not significantly different from one another. Furthermore, the low R-Index of GCT OD illustrates that its level of detection is at the chance-level, indicating a consumer likelihood of detecting this as different from a control formula (no tributyrin) is no higher than by chance.

In the R-Index by ranking test, R-Index scores range from 50 to 100 with higher numbers representing the increased likelihood of participants noticing that a sample is different from the noise. Estimated d' values show how different the sample is from the noise, with higher values indicating a greater difference. In certain embodiments, the products that are easily detectable as being different may be found to reside in the d' range of 1 and above. Results found that panelists were able to successfully identify both free and spray dried gamma-cyclodextrin encapsulated tributyrin as different from the "noise" plain infant formula. The high R-index and d' values showcased the large degree of difference the addition of these two forms of tributyrin cause to the infant formula matrix as compared to the noise. Results indicated that the addition of oven dried gamma-cyclodextrin encapsulated tributyrin caused a significant reduction in R-index value as compared to the spray dried form. This microencapsulate formulation brought the R-Index value down to 49.5. An R-index of about 50 would indicate that panelists were unable to detect a difference other than due to chance probability. Panelists were unable to detect a difference between the "noise" and the formula containing oven dried microencapsulated tributyrin in gamma-cyclodextrin. The estimated d' of 0 further illustrates the lack of difference between this sample and the noise.

Therefore, it can be concluded that the microencapsulation formulation of oven dried tributyrin and gamma-cyclodextrin was able to produce a particle with high retention and eliminate the sensory properties associated with native tributyrin. Being able to use tributyrin in a food application, such as infant formula, provides a facile medium to deliver this potentially health improving compound without the negative sensory attributes normally associated with it.

Example 3: Cyclodextrin Preparation

In order to produce microencapsulated tributyrin by oven drying using gamma-cyclodextrin, the following procedure may be implemented.

Gamma-cyclodextrin was mixed with water at about a 50% solids content and high-shear mixed for about 1 minute at about 8,000 RPM. Tributyrin at a molar ratio of about 3 moles of cyclodextrin to about 1 mole of tributyrin was added and mixed for about 20 minutes at about 8,000 RPM.

This mixture was allowed to sit at about room temperature for a total of about 26 hours. At about 6 hours into this process, the mixture was agitated briefly to re-suspend a two-phase mixture which may have begun to form. From this point on, the mixture was not agitated until the end of the total of about 26 hours. After about 26 hours, the two-phase mixture of cyclodextrin sediment and water layer of water was removed to provide a slurry. This slurry was then centrifuged for about 15 minutes at about 3000 RPM to remove the remaining water. After centrifugation the liquid phase was decanted and a solid (centrifugate) was collected. The solid phase was then spread evenly onto a glass surface in a relatively thin layer to form a product. The product was then placed into an oven at about 45° C. and allowed to dry for about 3-4 hours to form a dry product. After about 3-4 hours, the glass surface with dried product was removed from the oven. The product was scraped off the surface of the glass and ground into a find powder to form an inclusion complex. The moisture content of the inclusion complex was measured using a moisture content analyzer. Drying was complete when the powder had reached a moisture content of about 9-11%. If the inclusion complex did not fall within the moisture content specification, it was spread evenly as a powder onto a glass surface and placed back into the oven at about 45° C. for about 30-minute time intervals until the moisture content was reached Example 4: Comparative Testing of Butyrate In-vitro research was conducted wherein a complete digestion model (oral, stomach, and small intestine) and fermentation (large intestine) was implemented. The results are reported in terms of butyrate, rather than tributyrin, as the tests measured the butyrate that was released by the tributyrin. Tributyrin is composed of butyric acid, and in the digestive tract it can be broken down by digestive enzymes into butyrate or produced through fermentation. Butyrate is the primary energy source for epithelial tissue and bacteria throughout the digestive tract. Tributyrin comprising compositions are used as a source of butyric acid and tributyrin has been found to be particularly beneficial in the intestine.

Eight types of compositions were evaluated and the results are collected and reported below. In certain embodiments, the following compositions have been assigned acronyms for convenience and are represented in Table 3 below: WA, WAT, WAS, WAST, GC SD, GC OD, GCT SD, and GCT OD.

TABLE 3

Compositions

| Acronym | Composition |
| --- | --- |
| WA | Whey protein isolate and anhydrous milk fat |
| WAT | Whey protein isolate, anhydrous milk fat, and tributyrin |
| WAS | Whey protein isolate, anhydrous milk fat, and short chain inulin (7-9 repeating units of glucose) |
| WAST | Whey protein isolate, anhydrous milk fat, short chain inulin, and tributyrin |
| GC SD | Gamma-cyclodextrin, spray dried |
| GCT SD | Gamma-cyclodextrin, and tributyrin, spray dried (inclusion complex) |
| GC OD | Gamma-cyclodextrin, oven dried |
| GCT OD | Gamma-cyclodextrin and tributyrin, oven dried (inclusion complex) |

FIG. 1 shows the Percentage Release Total Butyrate Release. The figure shows that the majority of treatments released a majority (>70%) of butyrate within the small intestinal tract. In terms of physiological relevance to treatment, (Bartholome A L et. al., supra) stated that 9 mM treatment of butyric acid to small intestinal had most beneficial physiological effects to small intestinal structure and health. Therefore, about 12.5 g of GCT OD needs to be consumed per day for treatment. Each treatment of GCT OD contained about 2.5 g of powder equating to the need to consume about 5 servings (reasonable for infant formula, a nutritional shake, a fruit puree, or combination of both, for example).

Table 4 shows the amount of butyrate at each stage of delivery. The data demonstrates that GCT OD and GCT SD are gustatorily and olfactorily neutral and effective in targeting release of butyrate in the small intestine (DMB=Dry Matter Basis).

TABLE 4

Butyrate Amounts at Buffer, Stage 1 and Stage 2

| | mMol/g (DMB) | | |
| --- | --- | --- | --- |
| | Buffer | Stage 1 | Stage 2 |
| Tributyrin | 0.14 | 0.28 | 7.89 |
| WA | 0.00 | 0.00 | 0.19 |
| WAT | 0.03 | 0.04 | 1.35 |
| WAS | 0.00 | 0.00 | 0.13 |
| WAST | 0.03 | 0.04 | 1.29 |
| GC SD | 0.00 | 0.00 | 0.00 |
| GCT SD | 0.01 | 0.02 | 0.57 |
| GC OD | 0.01 | 0.00 | 0.00 |
| GCT OD | 0.01 | 0.03 | 0.72 |

Figure 2:
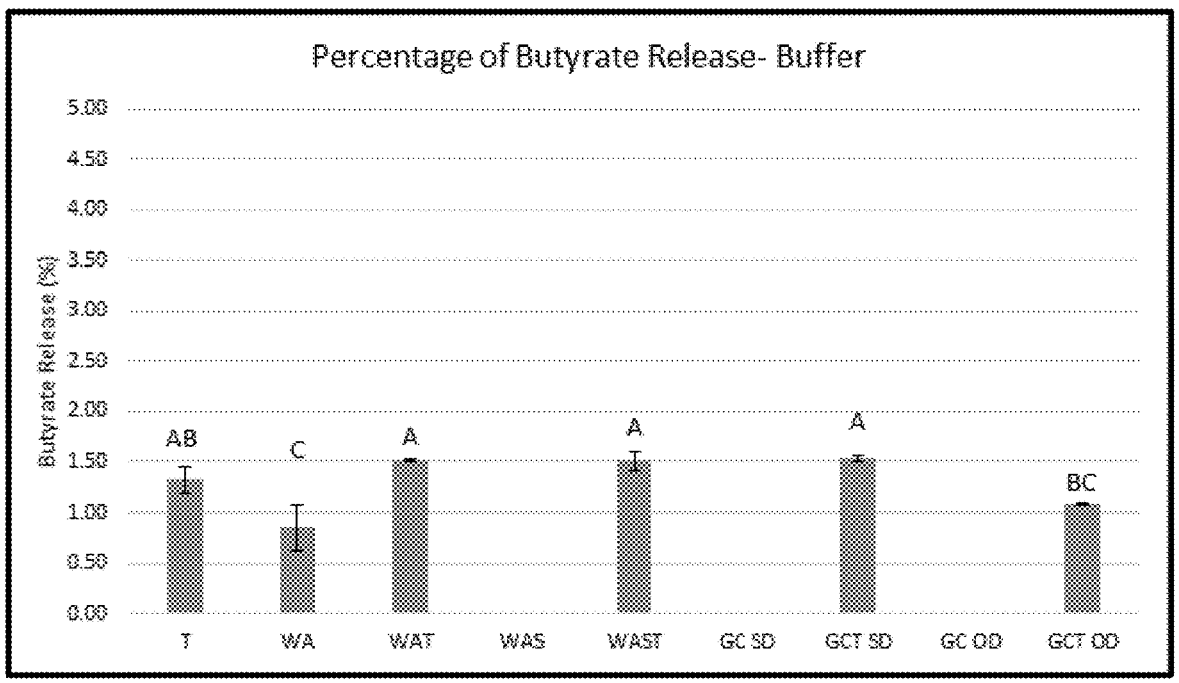
FIG. 2: Percentage of butyrate release in buffer (simulated oral phase).

FIG. 2 shows the Percentage of butyrate release in buffer (simulated oral phase). T, WAT, WAST, and GCT SD were not significantly different from each other. T and GCT OD were not significantly different from each other and WA and GCT OD were not significantly different from each other. GCT OD released significantly less butyrate than any other tributyrin comprising composition.

Figure 3:
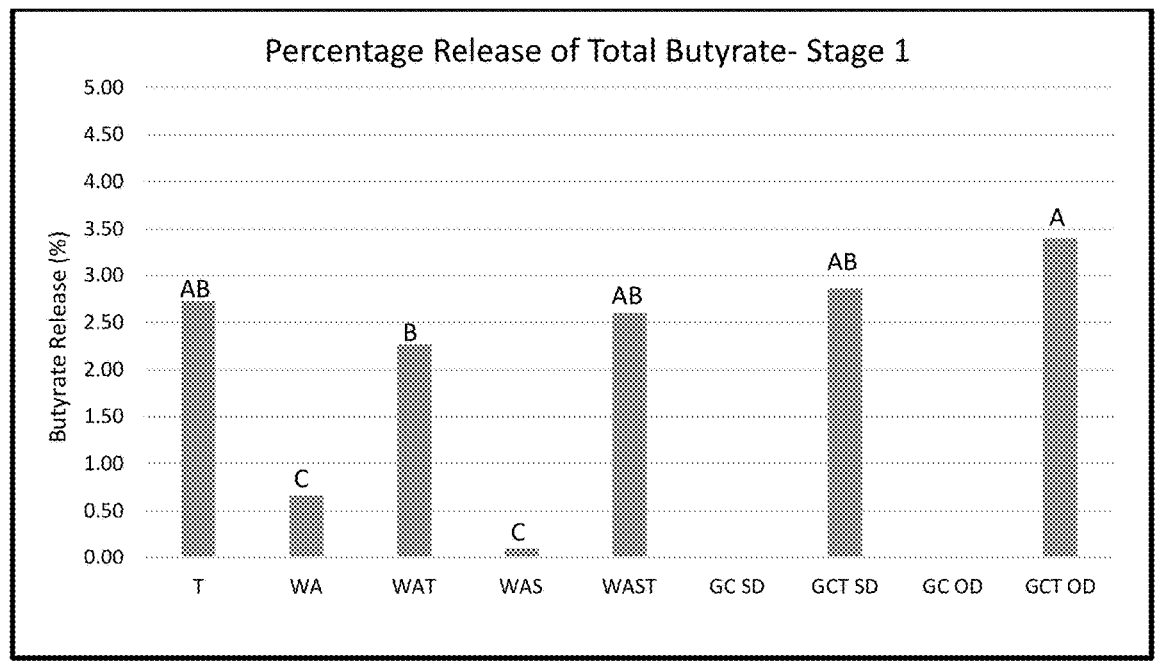
FIG. 3: Percentage release of total butyrate—stage 1.

FIG. 3 shows the Percentage release of total butyrate—stage 1. The results show that GCT OD, GCT SD, WAST, and free TB were not significantly different from each other in their release of tributyrin. WAT and GCT OD were significantly different from each other. None of the compositions have released >5% of the total tributyrin.

Figure 4:
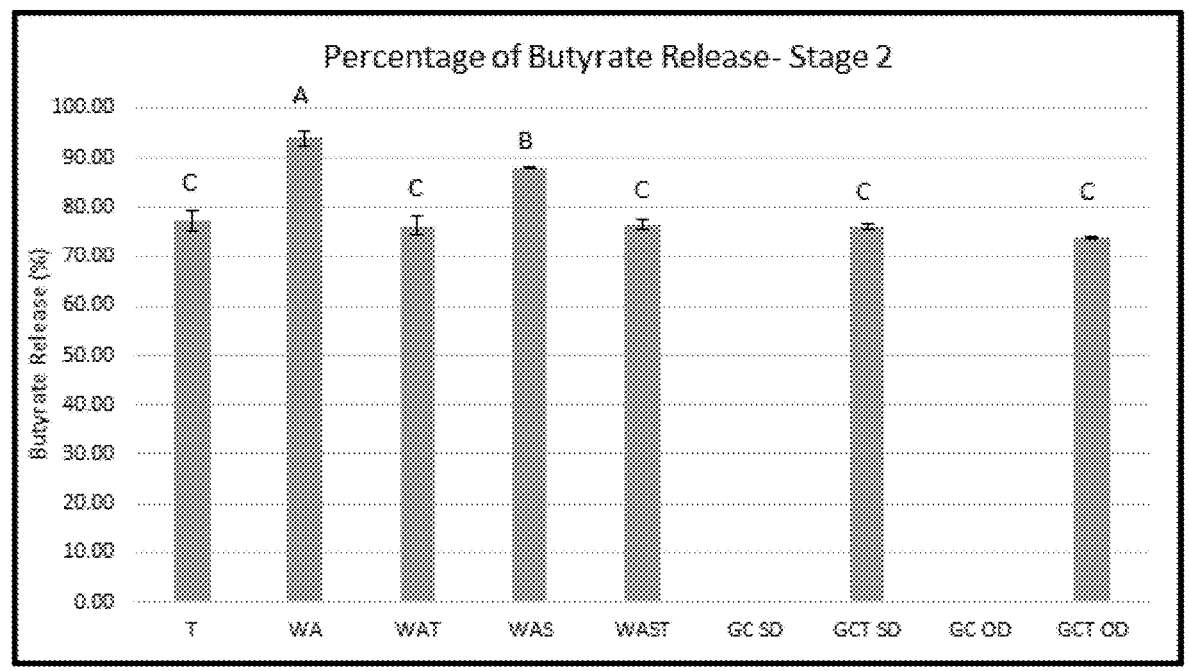
FIG. 4: Percentage release of total butyrate—stage 2.

FIG. 4 shows the Percentage release of total butyrate—stage 2. All tributyrin comprising compositions were not significantly different that one another in terms of the amount of total butyrate released at this stage. Control samples, WA and WAS, have essentially released all butyrate, while tributyrin comprising samples have released roughly 80% in total.

Figure 5:
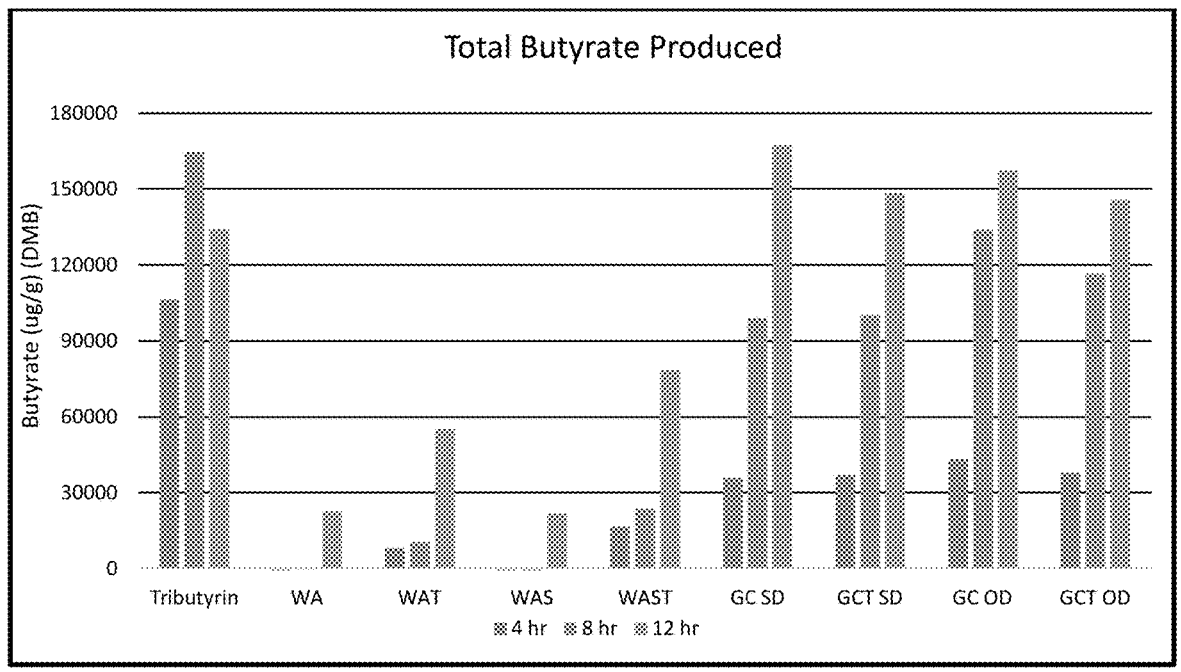
FIG. 5: Total Butyrate Produced (ug/g) Dry Matter Basis (DMB)

FIG. 5 shows the Total Butyrate Produced (μg/g). These results demonstrate that butyrate production significantly increased as fermentation continues. The data for FIG. 5 is shown in Table 5.

TABLE 5

Butyrate Amounts at 4 hr, 8 hr and 12 hr

| | Butyrate ug/g (DMB) | | |
|---|---|---|---|
| | 4 hr | 8 hr | 12 hr |
| Tributyrin | 106389.69 | 164605.74 | 134093.05 |
| WA | −1362.69 | −392.55 | 22536.18 |
| WAT | 8043.61 | 10366.81 | 55221.97 |
| WAS | −13232.1 | −16594 | 21728.69 |
| WAST | 16532.13 | 23566.68 | 78582.60 |
| GC SD | 35774.05 | 99051.05 | 167057.81 |
| GCT SD | 36928.62 | 100284.27 | 148369.42 |
| GC OD | 43191.49 | 133842.79 | 157190.56 |
| GCT OD | 37780.90 | 116524.03 | 145642.05 |

Figure 6:
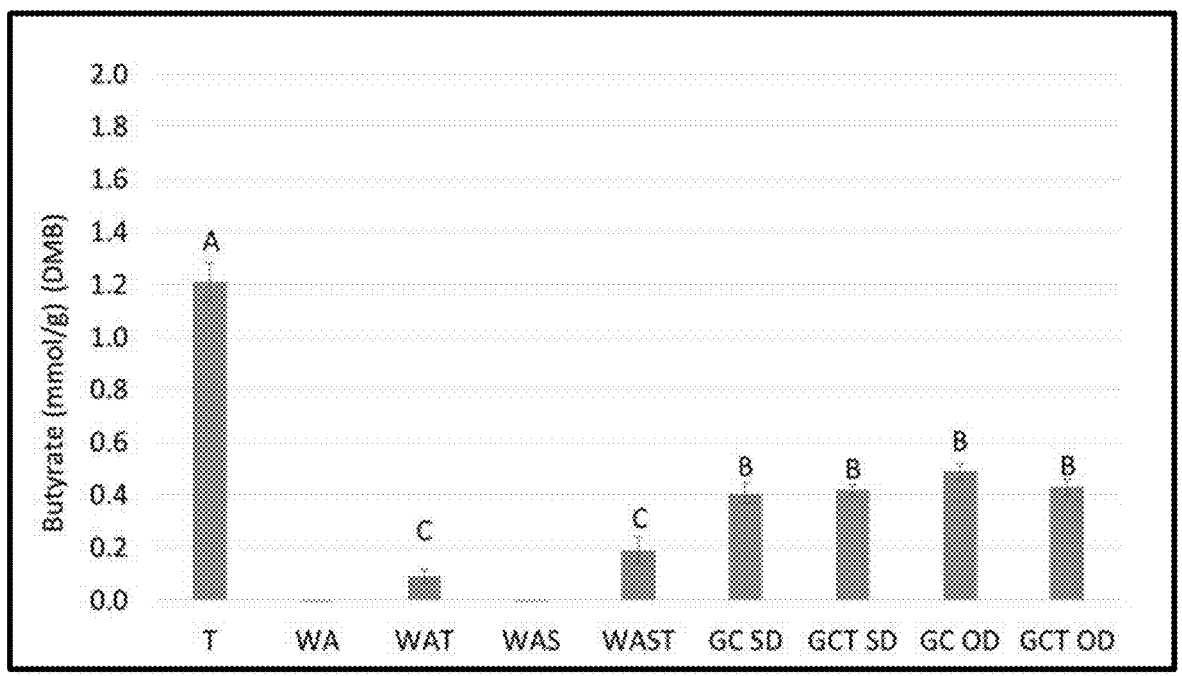
FIG. 6: Total Butyrate Produced (mmol/g) DMB—4 Hours.

FIG. 6 shows the Total Butyrate Produced—4 Hours. While tributyrin had significantly more butyrate production than all other tributyrin comprising compositions, it also began with much more on an ug/g basis, so the comparative focus could be better placed on the tributyrin comprising compositions WA and GCT OD. In comparing the tributyrin comprising compositions, the cyclodextrin based tributyrin comprising compositions performed significantly better than whey-based tributyrin comprising compositions in the production of butyrate at 4 hours. These data are representative of the "ascending" area of the large intestine.

Figure 7:
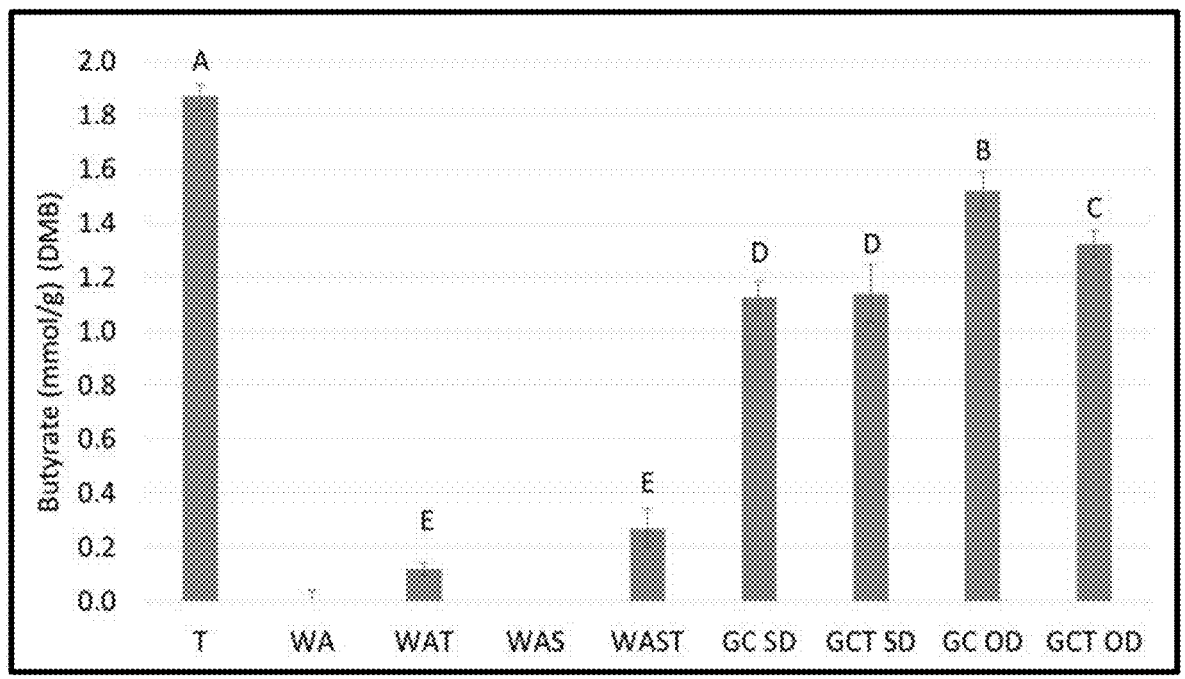
FIG. 7: Total Butyrate Produced (mmol/g) DMB—8 Hours.

FIG. 7 shows the Total Butyrate Produced—8 Hours.

Regarding the tributyrin comprising compositions, the cyclodextrin based composition without tributyrin is significantly higher than the one comprising tributyrin, however, the GCT OD is significantly higher than all other compositions comprising tributyrin. These data are representative of the "transverse" area of the large intestine.

Figure 8:
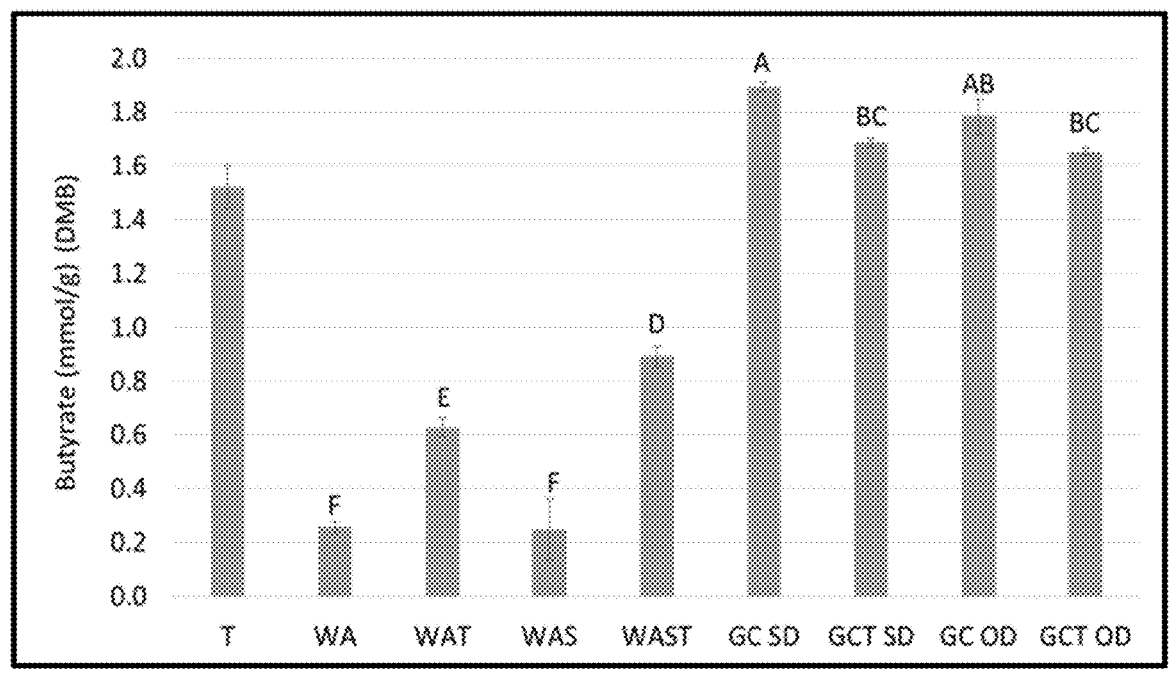
FIG. 8: Total Butyrate Produced (mmol/g) DMB—12 Hours.

FIG. 8 shows the Total Butyrate Produced—12 Hours. At this point in the large intestine, free tributyrin (labeled "Trybutyrin") no longer produced the most butyrate and is statistically non-significant compared to GCT SD and GCT OD. All cyclodextrin-based compositions produced significantly more butyrate than whey-based compositions. In terms of compositions, the spray-dried cyclodextrin based composition without tributyrin was significantly higher than the composition comprising tributyrin, however, the GCT OD was not significantly different than any other cyclodextrin-based composition. These findings show that the GCT OD (the best performing sensory composition) was able to produce significantly higher amounts of butyrate than whey-based compositions. These data are representative of the "descending" area of the large intestine.

Summary of Results

In the buffer stage (simulated oral phase), GCT OD has significantly less butyrate release than any other tributyrin containing capsule. This partially explains its improved sensory evaluation performance than previously seen. Considering the sensory data, GCT SD and all whey compositions performed poorly while GCT OD exhibited no difference from a control sample lacking any tributyrin.

The differences in tributyrin release (expressed as butyrate) between compositions during the first stages of digestion (oral, stomach, small intestine) were not significant with most compositions releasing roughly 80% of their contents in the small intestinal phase. This finding may demonstrate the use of these compositions as an effective way to administer physiologically relevant doses of butyrate to this area of the gut in the treatment of small intestinal disorders.

In the fermentation stage, all cyclodextrin comprising samples produced significantly more butyrate than any whey-based compositions making them better candidates for butyrate delivery and production.

GCT SD and GCT OD compositions produced significantly more butyrate than any whey-based capsule at all points of fermentation. At about hour 12, butyrate production was observed for all cyclodextrin based compositions. The butyrate level of T (free tributyrin) had begun to decrease as by this point it had been mostly used up. Note that the gamma-cyclodextrin compositions comprising tributyrin (GCT SD and GCT OD) exhibited no significant difference between one another; however, the sensory performance of GCT SD was as poor as all other compositions.

Therefore, considering sensory performance, digestive stability, and fermentative quality, GCT OD is able to deliver minimized sensory impact (olfactorily and gustorily neutral), digestive stability in the stomach with release in the small intestine, and butyrate production throughout all stages of the large intestine. This finding (helping small and large intestine) demonstrates that butyrate delivery to the descending colon is very challenging. The cyclodextrin tributyrin comprising compositions of the present disclosure benefit from providing to both these areas, unlike just eating plain GC SD or GC OD (which would produce butyrate in vivo through a fermentation process but have no effect in the small intestine).

Example 5: R-Index Ranking of Formulations in Infant Formula

The aim of this example was to determine the influence of an encapsulation method and the type of wall material on the sensory perception of tributyrin (TB). We utilized an R-index measure by rating method to determine the level at which panelists could detect the presence of various microencapsulated and free TB in an infant formula system. It is hypothesized that cyclodextrin (CD)-based microcapsules, due to their ability to complex core materials and reduce bitter sensory properties of other food ingredients, will provide an improved ability to mask the perception of TB in an infant formula.

Materials

Four different microcapsules containing tributyrin (TB) (tributyrin, 97% FG, Sigma-Aldrich Co. LLC, St. Louis, Mo.) were produced using varying combinations of WPI (Hilmar 9400, Hilmar Ingredients, Hilmar, Calif.), anhydrous milk fat (AMF) (Anhydrous Butter Oil, Dairy Farmers of America, Kansas City, Mo., USA), inulin (CLR, Sensus America, Inc., Lawrenceville, N.J.), and gamma-cyclodextrin (GCD) (CAVAMAX W8 Food, Wacker Chemie AG, München, Germany) to create the following four microcapsule formulations: WPI, AMF, with TB (WAT); WPI, AMF, and TB with short chain inulin (WAST); GCD and TB that was spray (GCT SD) or oven (GCT OD) dried.

Protein and Cyclodextrin-based Microcapsule Preparation and Quantification

All microcapsules were prepared according to the methods previously published in Donovan J D, Cadwallader K R, Lee Y, 2016, *Volatile retention and morphological properties of microencapsulated tributyrin varied by wall material and drying method*, J Food Sci (81 (3): E643-E650). Whey Protein Isolate (about 8% w/w) was dissolved in distilled water or a solubilized inulin solution (about 8% w/w) and agitated (Heidolph RZR 1 Mixer, Heidolph Instruments GmbH & Co. KG, Schwabach, Germany) at about 500-1,000 RPM to achieve a steady vortex. The solution was hydrated at about 25° C. and heated to about 80° C. for about 30 minutes (C76 Water Bath Shaker, New Brunswick Scientific, Enfield, Conn.). This solution was stored at about 4° C. for about 12 hours before a melted AMF-TB (about 8% AMF and about 3% (without inulin) or about 4% (with inulin) of TB, respectively) mixture was incorporated. The coarse emulsion then was run through a two-stage pressure homogenizer (SPX Flow Technology, Denmark) to create a stable homogenate for spray drying. Samples were then spray dried (Buchi Mini Spray Dryer B-290, BÜCHI Labortechnik AG, Flawil, Switzerland).

Gamma-cyclodextrin microcapsules were dissolved in distilled water at about a 50% solids content using the same high-shear mixer. Tributyrin was then added in a molar ratio of about 3:1 (GCD to TB) and agitated for about 20 minutes at about 8,000 RPM. The GCD-TB mixture sat at about 25° C. for about 26 hours in total before being transferred to an oven (Isotemp Incubator, Thermo Fischer Scientific, Inc., Waltham, Mass.) at about 46° C. for about 3.5 hours to dry or until a moisture content (HR83 Halogen Moisture Analyzer, Mettler-Toledo, LLC, Columbus, Ohio) of between about 8 and about 10% was achieved. The quantification of TB within each sample was determined using the methods outlined in Donovan, supra. All samples were quantified in this manner before their use in a formula to determine an equal amount of TB was added to each sample.

Sample Preparation

Specialized formulas are designed for those with a variety of intestinal maladies such as protein sensitive colitis, diarrhea, shortened bowel syndrome (Abad-Sinden A, Sutphen J, 2003, *Nutritional management of pediatric short bowel syndrome*, Pracat Gastroenterol., 28 (12):28-48) or nutrient malabsorption (*How EleCare and EleCare Jr Help* [Internet]: Abbott Laboratories, 2014 [Accessed Dec. 9, 2014] and available from: elecare.com/food-allergy-formula-products). One such formula is EleCare® Amino Acid-based Infant Formula with Iron (elecare.com), which is manufactured by Abbott Nutrition (Abbott Laboratories Inc., Abbott Park, Ill.). As mentioned previously, some of the intestinal maladies for which this formula is designed to be used have shown improved intestinal health with the use of butyrate. Therefore, this system should serve as a good model for the inclusion of the microcapsules.

Infant formula (EleCare® Amino Acid-based Infant Formula with Iron, Abbott Laboratories Inc., Abbott Park, Ill.) was prepared according to the package directions (about 18.8 g of powder per about 4 oz. water) with the specified amount of encapsulated or free TB as indicated in Table 6 below to reach a TB content equivalent to about 0.2 g TB/serving. Previous studies have observed physiological benefits using butyric acid in quantities of about 9 mmol (roughly about 0.79 g of butyric acid) in piglet intestinal models with induced SBS (Bartholome, supra). This concentration is also similar to the normal physiologic levels of butyric acid (Bartholome, supra).

The amount of TB/gram of particle in order to create the about 0.2 g TB/serving was determined using gas chromatography techniques described in Donovan, supra. Formula samples had the following variables added to them to make a total of six treatments: a blinded control or noise, free TB, WAT, WAST, GCT SD and GCT OD. The samples were prepared on the day of testing by vigorously shaking the encapsulate or free TB in infant formula for about 2 minutes. Samples (about 1.5 oz.) were poured into 2 oz. plastic soufflé cups and stored at about 4° C. before being served to panelists and were removed from the cold temperature about 30 minutes prior to testing to allow the samples to reach room temperature.

TABLE 6

Total amount of microencapsulated tributyrin added per serving of infant formula for the rating method to calculate the R-index measure

| Microcapsule formulation | Amount of tributyrin/ g of powder (g) | Amount of butyric acid/g of powder (g) | Amount added/ serving (g) | Total tributyrin content/ serving (g) | Total butyric acid content per serving (g) |
| --- | --- | --- | --- | --- | --- |
| Noise (control) | 0 | 0 | 0 | 0 | 0 |
| Free TB[1] | n/a | 0.17 | 0.20 | 0.20 | 0.17 |
| WAT[1] | 0.148 | 0.13 | 1.53 | 0.20 | 0.17 |
| WAST[1] | 0.162 | 0.142 | 1.41 | 0.20 | 0.17 |
| GCT OD[1] | 0.076 | 0.066 | 3.03 | 0.20 | 0.17 |
| GCT SD[1] | 0.051 | 0.045 | 3.88 | 0.20 | 0.17 |

[1]Free TB: unencapsulated tributyrin; WAT: whey protein isolate, anhydrous milk fat, tributyrin; WAST: whey protein isolate, anhydrous milk fat, short chain inulin, tributyrin; GCT OD: gamma-cyclodextrin and tributyrin oven dried; GCT SD: gamma-cyclodextrin and tributyrin spray dried.

Recruitment and Testing Procedures

All recruitment material, procedures, and testing materials were approved by the University of Illinois Institutional Review Board (IRB) (IRB Protocol Number: 4757). Panelists were recruited for the test through departmental listservs sent via-email. Panelists were required to complete a pre-screening survey to indicate if they qualified for the study. Panelists who were under the age of 18, had any food allergies, or lacked sufficient availability were disqualified from the study. The recruited subjects (n=33, 23 females, 10 males, aged 23-56) attended three, 20-minute testing sessions. The first half of the first session involved a brief introduction to the research objective, and the rating procedure to determine R-index measures.

Actual testing sessions were conducted in individual booths using red lighting to mask any possible color differences. Panelists recorded all responses using the Compusense five Plus (Version 5.0: Guelph ON, Canada) data acquisition system.

Panelists were presented with a sample labeled as the "noise". The noise in this study was the infant formula sample with no encapsulate or free TB added. Panelists were asked to acquaint themselves with the noise and were then presented with a tray of samples containing six, 2-oz plastic sample cups coded with 3-digit blinding codes. Panelists were asked to indicate if the coded sample was the same or different from the noise, and indicate how sure they were. They did this by selecting one of the following options: signal-sure; signal-unsure; noise-unsure; noise-sure. Panelists were required to expectorate all samples and rinses.

Between each sample, panelists rinsed with bread (¼ of a slice) (Bimbo soft white bread, Bimbo Bakeries USA, Inc., Horsham, Pa.), heavy whipping cream (5 oz. cup) (Ultra-pasteurized heavy whipping cream, Prairie Farms Dairy, Inc., Carlinville, Ill.), warm water (8 oz. cup) (about 43° C.), and room temperature water (8 oz. cup) (about 25° C.). All rinses were expectorated. The testing and rinsing procedure was repeated six times until all samples were evaluated. A total of five sample replications were completed for each panelist.

Statistical Analysis

The R-index measure was calculated by placing a panelist's responses into the response matrix (Table 7 below) and using the equation listed in Table 8 below (Brown, supra) to calculate the R-index. By summing the ratings for all sample replicates into an individual judge response matrix using equation 1 (where $n_s$=sum of signal ratings, and $n_n$=sum of noise ratings), individual judge R-index measures for each sample were calculated. Each individual R-index judge measure for each sample was then used to complete the analysis of variance (ANOVA) using the PROC ANOVA function of the Statistical Analysis Software (SAS)® Enterprise Guide® (Version 4.3, SAS Institute Inc., Cary, N.C.) to determine if significant differences (p<0.05) existed among the samples. If significant differences existed, the Least Significant Difference (LSD) test was conducted to determine where those differences laid.

TABLE 7

Response matrix used for calculating individual and pooled R-index measures

|  | SS | S? | N? | N |
|---|---|---|---|---|
| Signal | a | b | c | d |
| Noise | e | f | g | h |

TABLE 8

Equation used to calculate the R-index measure $$R\text{-index} = \frac{a(f+g+h) + b(g+h) + ch + \frac{1}{2}(ae + bf + cg + dh)}{n_s + n_n}$$

By combining all the responses, for all sample replicates, from all judges into a single response matrix per product, a value known as a pooled R-index was calculated. This value was compared to the chance level probability (50%) and using available tables (Bi and O'Mahony 2007) and set parameters ($\alpha$=0.01, two-tailed, and n=170), it was determined if a sample was significantly different from the noise. Individual and pooled R-index measures were tabulated using Microsoft Excel 2013 (Version 15.0: Microsoft Corporation, Redmond, Was.) while LSD calculations for the individual R-indices were done using XLSTAT (XLStat Pro 2015.1.01, Addinsoft SARL, New York, N.Y.).

Results and Discussion

Results showed there was a clear differentiation in the sensory perception of microencapsulated TB in the infant formula system. According to pooled R-index measures (Table 9 below), any R-index value over 57.95% was determined as significantly different from the control (Bi J, O'Mahony M, 2007, *Updated and extended table for testing the significance of the R-index*, J Sens Stud 22 (6):713-20.). The only microcapsule not significantly different from the control by this measure was GCT OD. Similar results were observed using the individual R-index measure (Table 10 below), with the GCT OD microcapsule being the only sample not significantly different from the control (p<0.001). All other microcapsules (WAT, WAST, and GCT SD) were significantly different from the control (p<0.05) and not significantly different (p>0.05) from free TB. This indicates that when TB was microencapsulated as a GCT OD in infant formula, the probability of it being viewed as different from the control is no greater than that of the chance probability. This demonstrates the ability of GCT OD to successfully reduce the sensory influence of TB making it indistinguishable from the noise. To explain why the results of GCT OD were significantly different from all other microcapsules, influences including processing method and microcapsule formulation must also be considered.

TABLE 9

Pooled ratings and R-index measures for all panelists, replications, and formulations

| Formulation | Signal sure responses | Signal unsure responses | Noise unsure responses | Noise sure responses | Calculated R-index[1] |
|---|---|---|---|---|---|
| Free TB[2] | 110 | 25 | 18 | 12 | 80.6** |
| WAT[2] | 110 | 20 | 24 | 11 | 80.3** |
| WAST[2] | 89 | 35 | 22 | 19 | 76.1** |
| GCT SD[2] | 77 | 30 | 32 | 26 | 71.6** |
| GCT OD[2] | 26 | 24 | 41 | 74 | 50.2 |
| Noise (control) | 29 | 15 | 48 | 73 | 50.0 |

[1]Values with ** indicate significant difference (p < 0.01) from the control as determined using the tables in Bi J, supra, where n = 170, $\alpha$ = 0.01, and two-tailed.
[2]Free TB: unencapsulated tributyrin; WAT: whey protein isolate, anhydrous milk fat, tributyrin; WAST: whey protein isolate, anhydrous milk fat, short chain inulin, tributyrin; GCT SD: gamma-cyclodextrin and tributyrin spray dried; GCT OD: gamma-cyclodextrin and tributyrin oven dried.

TABLE 10

Individual average R-index measures for all panelists, replications, and formulations

| Formulation | Average individual R-index[1] |
|---|---|
| Free TB[1] | 80.5[A]*** |
| WAT[1] | 80.2[A]*** |
| WAST[1] | 77.3[A]*** |
| GCT SD[1] | 72.8[A]*** |
| GCT OD[1] | 49.5[B]*** |
| Noise (control) | 50.0[B] |

[A] and [B]Samples that share the same superscript [A] or [B] are not significantly (p < 0.001 or ***) from one another.
[1]Free TB: unencapsulated tributyrin; WAT: whey protein isolate, anhydrous milk fat, tributyrin; WAST: whey protein isolate, anhydrous milk fat, short chain inulin, tributyrin; GCT SD: gamma-cyclodextrin and tributyrin spray dried; GCT OD: gamma-cyclodextrin and tributyrin oven dried.

The difference in sensory perception exhibited by the different microcapsules may be partially explained by the processing method utilized to create the microcapsules. During spray drying, a matrix style microcapsule is most commonly produced (Sheu, Rosenberg, 1995, *Microencapsulation by spray drying ethyl caprylate in whey protein and carbohydrate wall systems*, J Food Sci 60 (1):98-103; Sheu, Rosenberg, 1998, *Microstructure of microcapsules consisting of whey proteins and carbohydrates*, J Food Sci 63 (3):491-4; Hogan et al., 2001, *Emulsification and microencapsulation properties of sodium caseinate/carbohydrate blends*, Int Dairy J 11 (3):137-44). This type of structure is produced during the expansion and contraction of the particle feed during drying. The evaporation of moisture in the system causes the expansion of the particle leaving a central void. During cooling, the contraction and formation of the dried wall layer occurs (Gharsallaoui, supra) creating a circular structure. This hollow interior creates small pockets containing the encapsulated ingredient to form alongside the microcapsule wall surface. Differences in the presence of surface or near-surface TB in spray dried microcapsules can influence their sensory perceptions. With the strong taste qualities of TB, a close proximity of this compound to the surface may allow for its facilitated release in the oral cavity and food matrix leading to an increased perception of TB. This may explain why panelists identified all spray dried formulations in the study as significantly different from the control.

Contrary to these results, previous results reported in the literature have used spray drying as a successful method to reduce or isolate compounds with negative taste active properties (Bora et al., *Taste Masking by Spray-Drying Technique*, 2008, AAPS PharmSciTech 9.4:1159-1164; Molina Ortiz et al., 2009, *Production and properties of casein hydrolysate microencapsulated by spray drying with soybean protein isolate*, LWT-Food Sci Technol 42 (5):919-923; Kawakami et al., 2009, *Formation of rice flavor powder with α-cyclodextrin by spray drying*, Eur Food Res Technol 229 (2):239-245). This inconsistency suggests that potential adjustment of parameters related to spray drying (i.e., inlet/out temperature, flow rate, pressure, etc.) and formulation (i.e., solids content, viscosity, wall materials, etc.) may allow for the successful encapsulation of TB using spray drying as a method to reduce the sensory impact of TB in food systems.

Aside from the processing method, the microcapsule formulation may also play a significant role in the ability of the microcapsules to reduce the sensory influence of TB. Cyclodextrins are commonly used to mask off tastes and odors in food products. Utilizing the same formulation (50% solids, 3:1 GCD to TB ratio) as GCT OD, GCT SD performed essentially identically to WAT and WAST in the R-index measure by rating test. Contrary to GCT OD, using CDs offered no benefit over WPI-based microcapsules for the GCT SD microcapsule. The poor retentive qualities of a spray dried cyclodextrin may be the result of sub-optimal spray drying conditions in GCT SD.

It has been previously hypothesized that the complex of a spray dried cyclodextrin is damaged by its exposure to high temperatures during spray drying (Bhandari et al., 1998, *Lemon oil to β-cyclodextrin ratio effect on the inclusion efficiency of β-cyclodextrin and the retention of oil volatiles in the complex*, J Agric. Food Chem. 46 (4):1494-1499; Reineccius et al., 2002, *Encapsulation of flavors using cyclodextrins: comparison of flavor retention in alpha, beta, and gamma types*, J Food Sci 67 (9):3271-3279; Reineccius et al., 2004, *Utilization of β-Cyclodextrin for improved flavor retention in thermally processed foods*, J Food Sci 69 (1):FCT58-62; Hădărugă et al., 2006, *Thermal stability of the linoleic acid/α- and β-cyclodextrin complexes*, Food Chem. 99 (3):500-508; Kawakami et al., 2009, *Formation of rice flavor powder with α-cyclodextrin by spray drying*, Eur Food Res Technol 229 (2):239-245). The high solids content of GCT SD may have led to ineffective atomization and delayed particle formation during the hottest inlet drying temperatures (Reineccius, supra). The heat-damaged complexation may have released TB. This release may be what caused the GCT SD to behave no differently from free TB when it was included into the formula. If the TB in GCT SD had remained in complex with GCD, like it did in GCT OD, it likely would have had the same improved taste masking ability as GCT OD. Therefore, GCT SD's sensory performance supports the hypothesis that the GCD-TB complex was damaged during drying and caused the release of TB that was perceived by the panelists.

While GCD complexation has not been analytically confirmed, it is assumed that complexation of TB is created and maintained in the GCT OD formulation due to its performance in the rating test. While CDs can provide some taste masking ability without any prior complexation (referred to as "empty CDs" addition) (Szente and Szejtli, supra), this is likely not the primary mechanism that GCT OD utilized in reducing the sensory impact of TB in the infant formula. If this was the mechanism of taste masking seen in GCT OD, the microcapsule should have performed essentially identically to GCT SD, since they each contained identical amounts of GCD. Further research could investigate the nature of the GCD and TB complexation utilizing analytical techniques, such as high performance liquid chromatography (HPLC), nuclear magnetic resonance (NMR), differential scanning calorimetry (DSC), or other spectroscopy methods, such as Fourier transform (FT)-Raman, FT-infrared and ultraviolet-visible (UV-VIS) (Hedges, supra; Das et al., 2013, *Cyclodextrins—the molecular container*, Res J Pharm Biol Chem Sci 4 (2): 1694-1720).

The importance of sensory testing in the evaluation of microencapsulated materials is apparent throughout the research. While understanding the TB retentive ability of microcapsules is important, the R-index measures that were found here suggest that TB retention was not indicative of how well an encapsulated system can isolate a core material from the targeted food system. Microcapsules with similar retention values (Table 11 below) had dramatic differences in sensory perception in the rating method. Significant differences ($p<0.05$) in retention were observed between WAST microcapsules and WAT and GCT SD, with GCT SD retaining the least TB. However, all three of the microcapsules were not significantly different ($p>0.05$) among one another or in comparison to free TB in R-index measures. Therefore, the level of TB retention in a microcapsule may not be a strong indicator of an improved isolation and/or protection of the core material, and in fact, may be immaterial to determining the isolation/protection properties. Therefore, the success of a microcapsule formulation on the isolation/protection of a compound cannot be determined on retention alone, and one should consider other stability factors, one of which is sensory testing (Lee Y, Lee S, Donovan J D, 2014, Chapter 28—*Stability characterization and sensory testing in food products containing microencapsulants*, in: Anilkumar et al., eds., *Microencapsulation in the Food Industry*, San Diego, Academic Press, pp 367-381).

TABLE 11

Average estimated tributyrin content and retention based on microcapsule drying method and formulation

| Sample | Drying method | Average estimated tributyrin content (g TB/g powder)[1] (±SEM)[2] | Optimal tributyrin content[3] (g TB/g powder) | Average retention (%)[4] |
|---|---|---|---|---|
| GCT[5] | SD | 0.051 ± 0.002 | 0.082 | 61.93 ± 1.61[A] |
| WAT[5] | SD | 0.148 ± 0.003 | 0.183 | 81.06 ± 1.90[C] |
| WAST[5] | SD | 0.162 ± 0.002 | 0.185 | 87.72 ± 0.927[D] |
| GCT[5] | OD | 0.076 ± 0.001 | 0.080 | 94.58 ± 1.10[E] |

[1] All observed averages are derived from six measurements taken from two experimental replicates.
[2] Samples with the same letter are not significantly different ($\alpha > 0.05$) from one another.
[3] Standard error of the mean.
[4] Optimal tributyrin content is based on microcapsule formulation and moisture content of each microcapsule tested.
[5] WAT: whey protein isolate, anhydrous milk fat, tributyrin; WAST: whey protein isolate, anhydrous milk fat, tributyrin, short chain inulin; GCT: gamma-cyclodextrin and tributyrin; SD: spray dried; OD: oven dried.

CONCLUSIONS

We have determined that an oven dried microencapsulation formulation of TB using GCT OD produced a stable inclusion complex that was able to reduce the sensory perception of TB to a level that was indistinguishable from a control infant formula without TB. This finding allows one to facilely administer an important bioactive component through food delivery. The non-digestible nature of GCD holds promise for its ability to enable the targeted delivery of this compound to areas of the intestinal tract necessary for those suffering from intestinal disorders The microcapsules WAT, WAST, and GCT SD produced significantly different results from the control formula for both pooled and individual R-index measures. The poor results for WAT and WAST may stem from the matrix style structured capsule produced during the spray drying process, which allows for surface TB to be perceived by the panelists. The spray-dried whey protein formulations provide matrix style microcapsules, rather than the chemical complexation microcapsules provided by GCT OD. Oven drying and grinding of whey protein formulations would likely produce a powder having a large amount of surface area, which could expose the tributyrin. Additionally, having a lower amount of solids, an oven dried whey protein formulation would likely take a significantly longer time to dry or require the application of a much higher temperature to reach a moisture content range similar to that of an oven dried gamma-cyclodextrin formulation.

An extended drying time could lead to spoilage and growth of bacteria in the protein-rich matrix if the temperature is kept low enough, or disrupt the complex if the temperature is raised too high. The whey protein formulations will always make a matrix-style microcapsule, which means the particles will possess a more physical than chemical separation. Therefore, regardless of the drying method, whey protein formulations will likely have high amounts of tributyrin dispersed throughout the entire particle, some of which reside near the surface and can be liberated upon dissolution, since the compound is not chemically bonded.

It is not readily apparent why GCT SD performed so poorly. The unsuccessful ability of GCT SD to reduce sensory qualities of TB in the infant formula may stem from heat-induced complexation disruption, due to the drying parameters and high solids content of the formulation, which could lead to complexation disruption and the release of TB. It may also relate to the particular formulation or particular process conditions used in the examples. For whatever reason, the formulation of GCT SD described above did not provide a stable complexation microcapsule like was provided by GCT OD. Modifications to the spray drying process to improve the performance of the spray-dried GCD formulations are being investigated.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A stable inclusion complex comprising tributyrin and γ-cyclodextrin, wherein the molar ratio of tributyrin to γ-cyclodextrin consists of about 1:1 to about 1:3 and the inclusion complex is olfactorily and gustorialy neutral in comparison to free tributyrin wherein tributyrin is encapsulated by γ-cyclodextrin to form a solid inclusion complex.

2. The stable inclusion complex of claim 1 wherein the solid inclusion complex is not degraded at forming the solid inclusion complex.

3. The stable inclusion complex of claim 1 wherein the solid inclusion complex has a water content of about 9% to about 11% by weight.

4. The stable inclusion complex of claim 1 wherein the solid inclusion complex is a dry product.

5. The stable inclusion complex of claim 4 wherein the solid inclusion complex has been dried at about 45° C. for at least 3 hours.

6. A stable inclusion complex comprising tributyrin and γ-cyclodextrin, wherein the molar ratio of tributyrin to γ-cyclodextrin is about 1:1 to about 1:3 and the inclusion complex is olfactorily and gustorialy neutral in comparison to free tributyrin wherein the inclusion complex is oven dried.

7. A food additive comprising the inclusion complex of claim 1 and a dietary acceptable supplement.

8. The food additive of claim 7 further comprising calcium, at least one natural flavor, at least one sweetener, at least one disintegrant, at least one protein, at least one carbohydrate, at least one other mineral, at least one vitamin, or at least one organic acid.

9. The food additive of claim 7 wherein the supplement comprises an omega-3 fatty acid, Vitamin A, Vitamin D3, Vitamin E, or a combination thereof.

10. An oral infant formula comprising the inclusion complex of claim 1 and one or more of milk, water, a protein, a carbohydrate or sugar, a mineral, a vitamin, or an edible fat.

11. A method of preparing the stable inclusion complex according to claim 1, comprising:

a) mixing trubutyrin and γ-cyclodextrin in water to form a first inclusion complex; and b1) drying the first inclusion complex for a sufficient period of time to form a stable inclusion complex at a temperature that does not degrade the stable inclusion complex; or b2) drying the first inclusion complex for a sufficient period of time to form a stable inclusion complex that has a moisture content of less than about 11%;

wherein the stable inclusion complex has a taste and odor that is indistinguishable from a γ-cyclodextrin that does not comprise tributyrin.

12. A method of inhibiting an inflammatory bowel disease or disorder comprising administering a therapeutically effective amount of the stable inclusion complex of claim 1 to a subject in need thereof.

13. The method of claim 12 wherein the inflammatory bowel disease or disorder comprises ulcerative colitis, Crohn's disease, irritable bowel syndrome, shortened bowel syndrome, or a combination thereof.

14. A method of inhibiting colon cancer comprising administering a therapeutically effective amount of the stable inclusion complex of claim 1 to a subject in need thereof.

15. A method of relieving food deficiency comprising administering a therapeutically effective amount of the stable inclusion complex of claim 1 to a subject in need thereof.

16. The method of claim 15 wherein the therapeutically effective amount is about 12.5 g per day.

17. The stable inclusion complex of claim 1 wherein the molar ratio of tributyrin to γ-cyclodextrin is 1:2.

\* \* \* \* \*